(12) United States Patent
Shimada

(10) Patent No.: US 10,240,982 B2
(45) Date of Patent: Mar. 26, 2019

(54) MEASUREMENT SYSTEM, INFORMATION PROCESSING APPARATUS, INFORMATION PROCESSING METHOD, AND MEDIUM

(71) Applicant: CANON KABUSHIKI KAISHA, Tokyo (JP)

(72) Inventor: Takuya Shimada, Utsunomiya (JP)

(73) Assignee: Canon Kabushiki Kaisha, Tokyo (JP)

(*) Notice: Subject to any disclaimer, the term of this patent is extended or adjusted under 35 U.S.C. 154(b) by 248 days.

(21) Appl. No.: 15/409,415

(22) Filed: Jan. 18, 2017

(65) Prior Publication Data

US 2017/0205291 A1    Jul. 20, 2017

(30) Foreign Application Priority Data

Jan. 20, 2016 (JP) ................. 2016-009305
Jan. 20, 2016 (JP) ................. 2016-009310
Nov. 8, 2016 (JP) ................. 2016-218206
Nov. 8, 2016 (JP) ................. 2016-218207

(51) Int. Cl.
*H04N 7/18* (2006.01)
*G01J 9/00* (2006.01)
*H04N 5/225* (2006.01)
*G01N 21/47* (2006.01)
*G01N 21/57* (2006.01)

(52) U.S. Cl.
CPC ............ *G01J 9/00* (2013.01); *G01N 21/4738* (2013.01); *G01N 21/57* (2013.01); *H04N 5/2256* (2013.01)

(58) Field of Classification Search
CPC ....... G01J 9/00; G01N 21/57; G01N 21/4738; H04N 5/2256

USPC ......................................... 348/143
See application file for complete search history.

(56) References Cited

U.S. PATENT DOCUMENTS

| 6,850,275 B1* | 2/2005 | Minakami ............ H04N 5/142 348/252 |
| 2002/0071124 A1 | 6/2002 | Schwarz |
| 2009/0097033 A1 | 4/2009 | Kuusela |
| 2014/0071459 A1* | 3/2014 | Nakatsukasa .......... G01B 11/25 356/611 |
| 2014/0192162 A1* | 7/2014 | Aoki ..................... G02B 7/34 348/46 |
| 2014/0340707 A1 | 11/2014 | Hirabayashi et al. |

FOREIGN PATENT DOCUMENTS

JP       2008-249521 A    10/2008
WO       98/49541 A1      11/1998

* cited by examiner

*Primary Examiner* — Allen C Wong
(74) *Attorney, Agent, or Firm* — Canon U.S.A., Inc., IP Division

(57) ABSTRACT

A measurement apparatus includes an illumination unit configured to illuminate a measurement object with use of a plurality of point light sources configured to emit light based on illumination images modulated according to periodic functions out of phase with one another, an imaging unit configured to image the measurement object illuminated based on the illumination images, a first calculation unit configured to calculate phase information of a change in a luminance value at each of pixels based on a plurality of images captured by the imaging unit, and a first acquisition unit configured to acquire, from the phase information, a maximum reflection direction where a reflection direction is maximized on the measurement object.

23 Claims, 33 Drawing Sheets

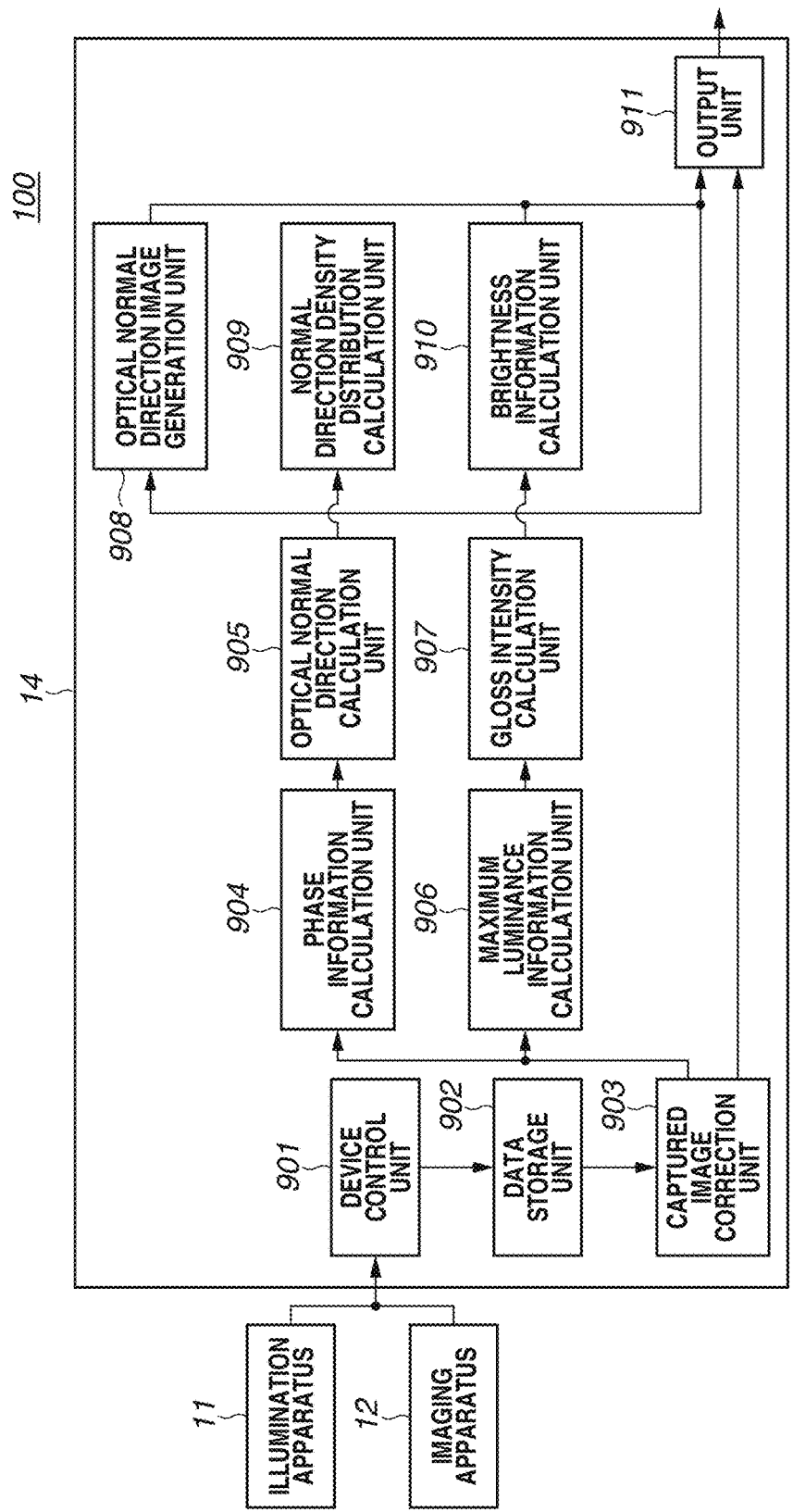

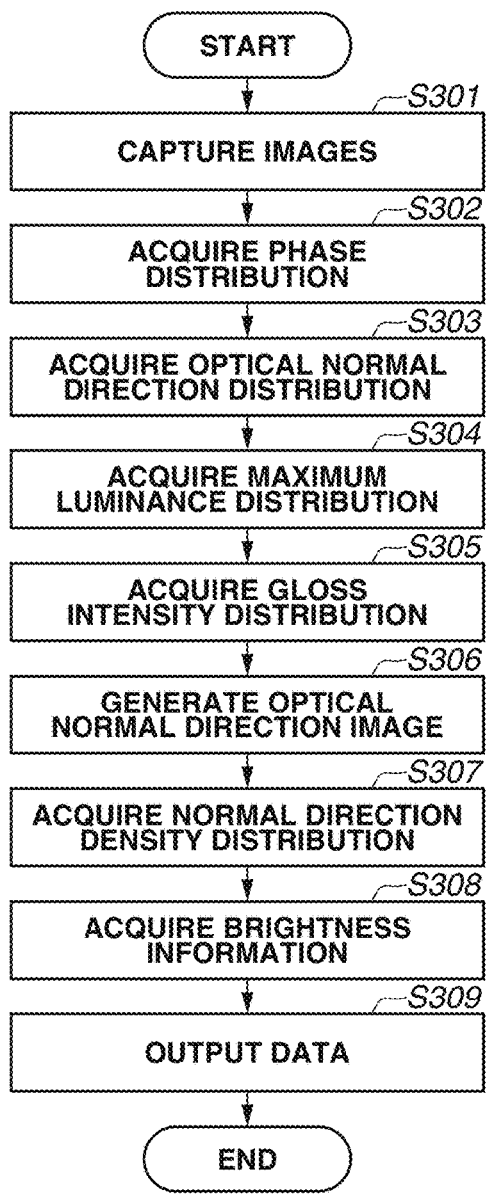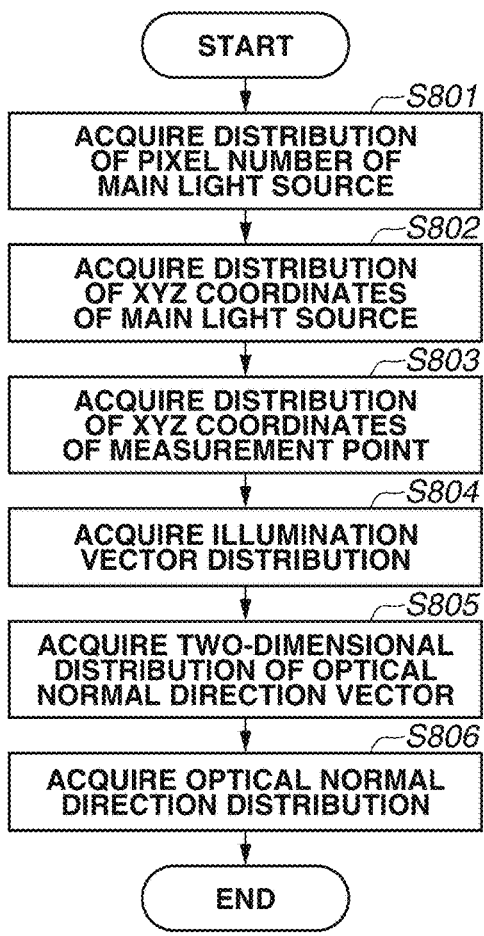

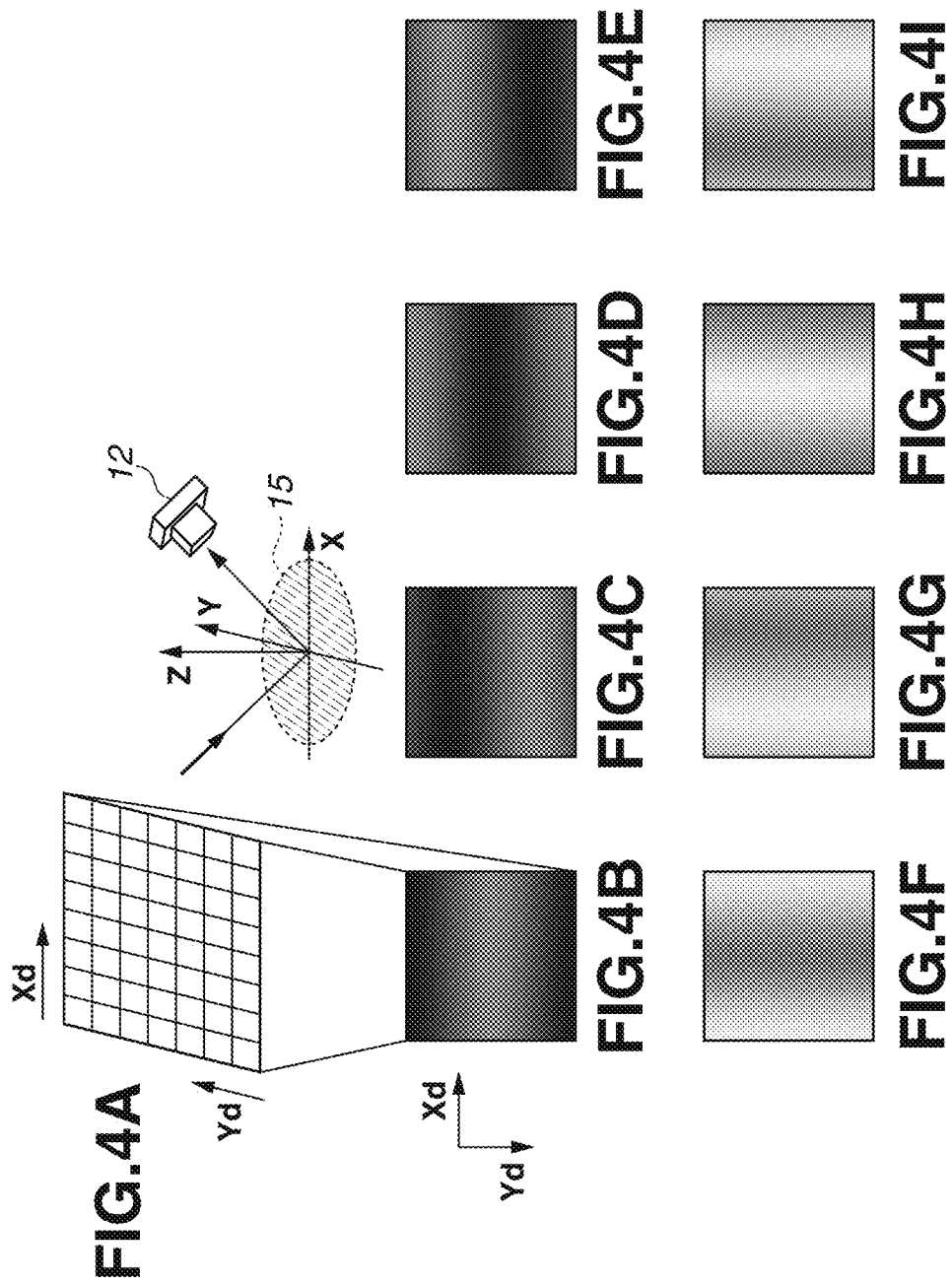

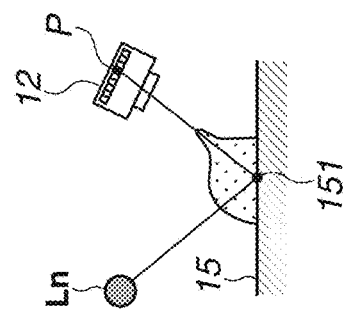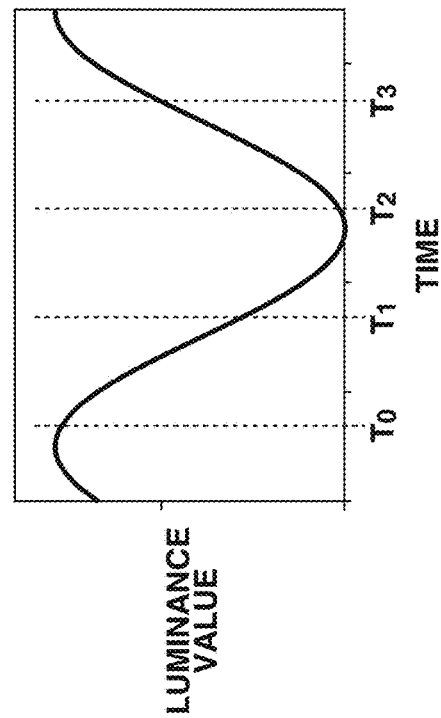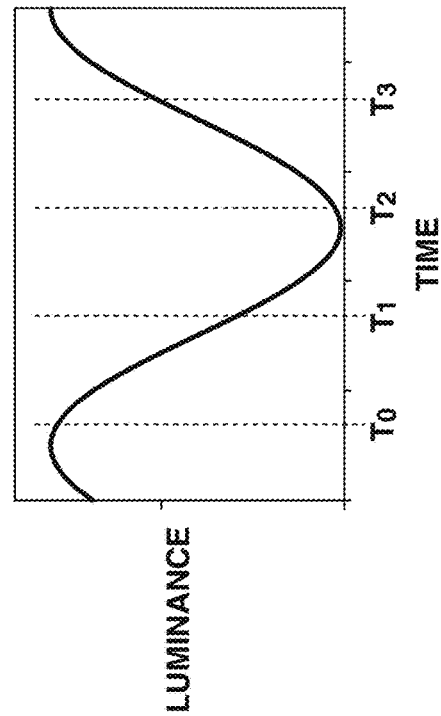

FIG.10

| MAXIMUM LUMINANCE INFORMATION D | SPECULAR GLOSSINESS |
|---|---|
| 32 | xx |
| 48 | xxx |
| . | . |
| . | . |
| . | . |
| 224 | xxx |
| 240 | xxx |
| 255 | xxx |

FIG.12

| NORMALIZED REFLECTION INTENSITY Icor | PHASE INFORMATION |
|---|---|
| -1 | 180 |
| -0.95 | 161.8 |
| . | . |
| . | . |
| . | . |
| 0.9 | 25.8 |
| 0.95 | 18.2 |
| 1 | 0 |

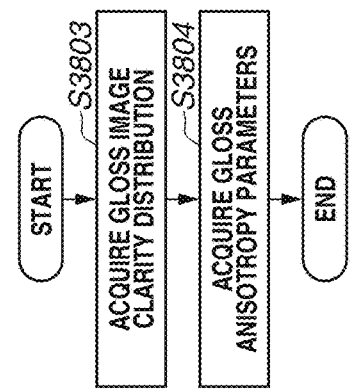
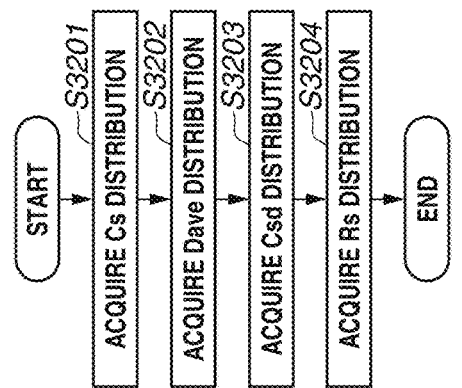
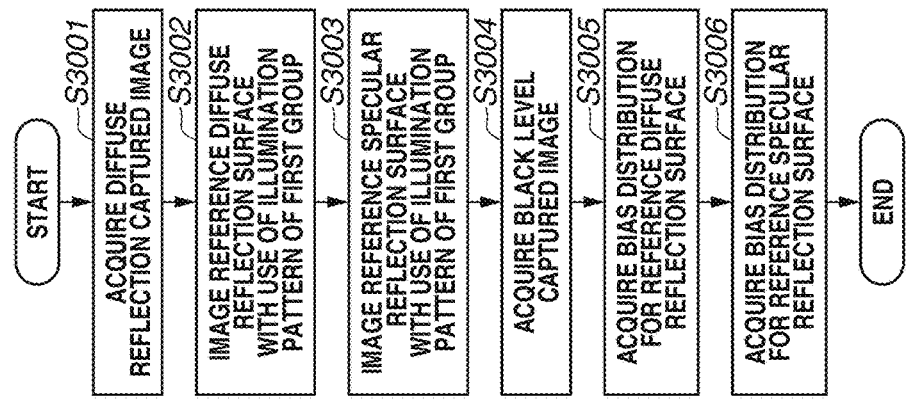
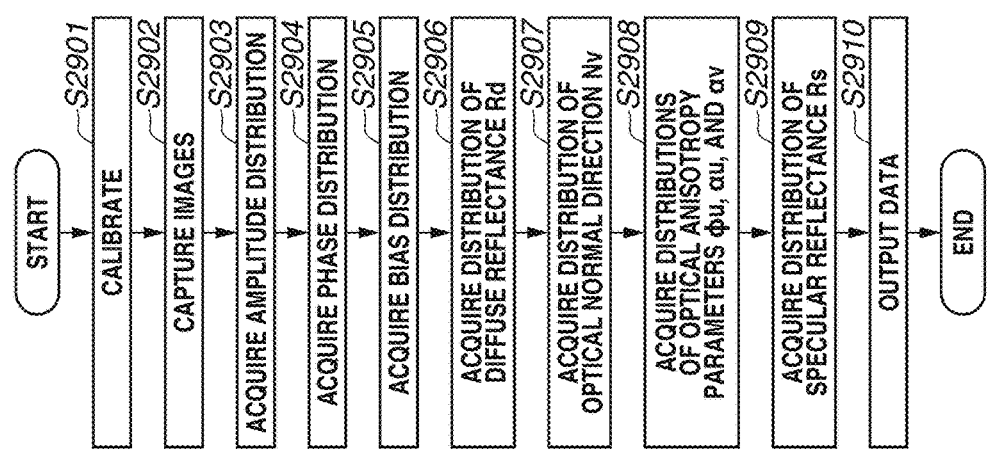

FIG.28A

| GLOSS IMAGE CLARITY αu | GLOSS IMAGE CLARITY αv | Dave |
|---|---|---|
| 0.01 | 0.01 | xx |
| 0.01 | 0.1 | xx |
| 0.01 | 0.2 | xx |
| . | . | . |
| 0.01 | 1 | xx |
| 0.1 | 0.01 | xx |
| . | . | . |
| . | . | . |
| 1 | 1 | xx |

FIG.28B

| AMPLITUDE INFORMATION | GLOSS IMAGE CLARITY |
|---|---|
| 0 | 0 |
| 16 | 10 |
| . | . |
| . | . |
| . | . |
| 96 | 74 |
| 112 | 86 |
| 128 | 98 |

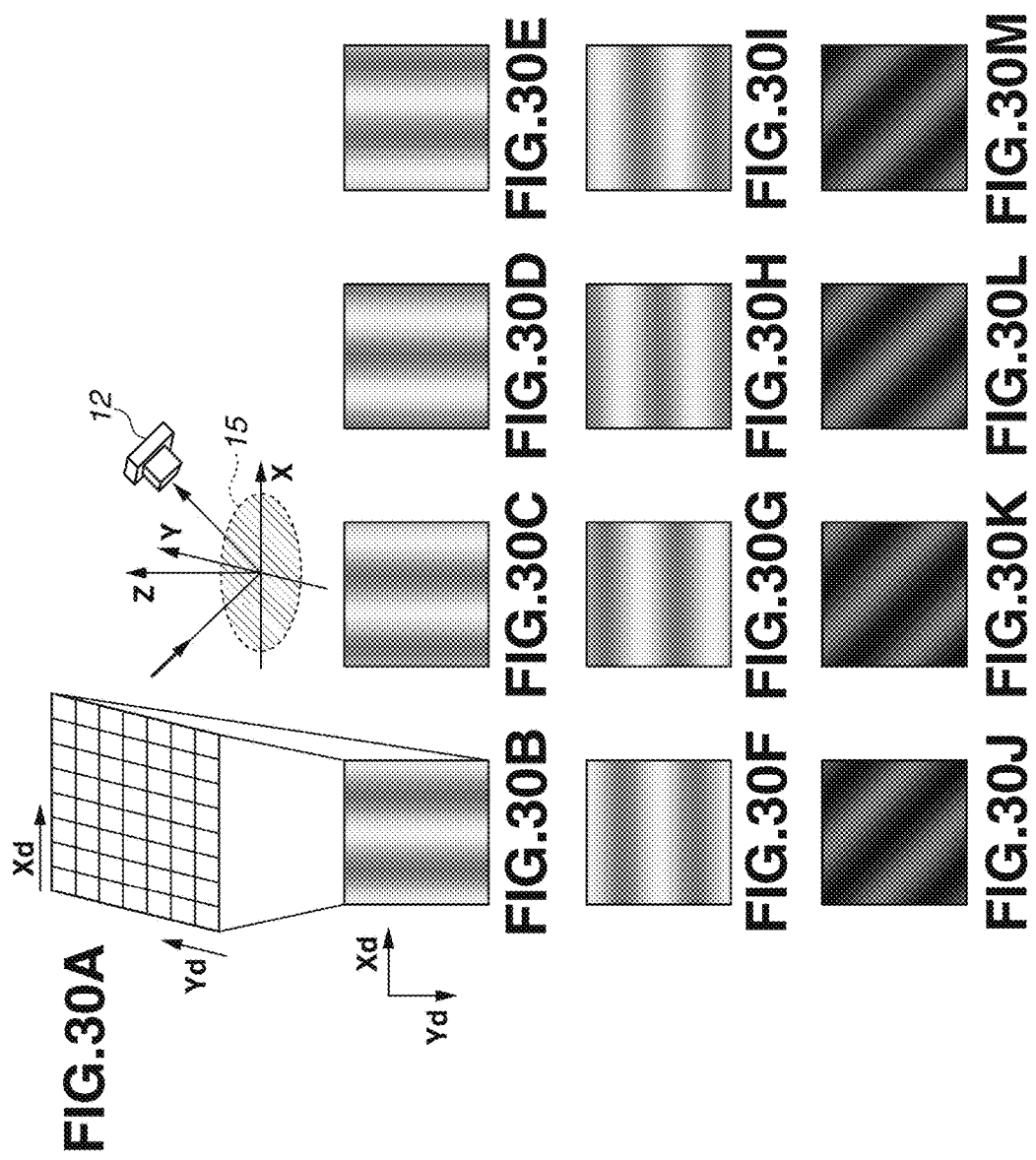

MEASUREMENT SYSTEM, INFORMATION PROCESSING APPARATUS, INFORMATION PROCESSING METHOD, AND MEDIUM

BACKGROUND OF THE INVENTION

Field of the Invention

The present invention relates to a technique for measuring an optical characteristic of an object.

Description of the Related Art

Some objects have a surface that appears differently according to an illumination direction of a light source and an observation direction. This is because reflected light leading from light with which the surface of the object is irradiated has a different characteristic according to the illumination direction and the observation direction. Therefore, there is widely known a technique for measuring a reflection characteristic of such an object. Japanese Patent Application Laid-Open No. 2008-249521 discusses a method that measures reflected light at a plurality of angles. First, a measurement apparatus drives a light reception unit to scan within a predetermined region corresponding to a position of a light source, and identifies a position of specular reflected light where a received light amount is maximized. Then, the measurement apparatus determines a plurality of measurement positions based on the identified position of the specular reflected light, and measures the light while moving the light reception unit, thereby detecting a reflection characteristic of a measurement target.

However, according to the method discussed in Japanese Patent Application Laid-Open No. 2008-249521, a mechanism, such as a motor and an arm, is necessary to set the light reception unit at a plurality of positions, thereby leading to a complicated configuration.

SUMMARY OF THE INVENTION

Therefore, the present invention is directed to measuring a reflection characteristic of an object with a further simple configuration which does not require a mechanism for moving a position of a light source and a position of a light reception unit.

According to an aspect of the present invention, a measurement apparatus includes an illumination unit configured to illuminate a measurement object with use of a plurality of point light sources configured to emit light based on illumination images modulated according to periodic functions out of phase with one another, an imaging unit configured to image the measurement object illuminated based on the illumination images, a first calculation unit configured to calculate phase information of a change in a luminance value at each pixel based on a plurality of images captured by the imaging unit, and a first acquisition unit configured to acquire, from the phase information, a maximum reflection direction where a reflection direction is maximized on the measurement object.

Further features of the present invention will become apparent from the following description of exemplary embodiments with reference to the attached drawings.

BRIEF DESCRIPTION OF THE DRAWINGS

FIGS. 2A and 2B are block diagrams illustrating a configuration of an information processing apparatus according to the first exemplary embodiment.

FIGS. 3A and 3B are flowcharts illustrating processing according to the first exemplary embodiment.

FIGS. 4A to 4I are schematic views illustrating an example of illumination images according to the first exemplary embodiment.

FIGS. 5A, 5B, and 5C are schematic views illustrating a relationship between a point light source and a light-receiving element.

FIG. 10 is a diagram illustrating an example of a gloss intensity conversion table.

FIG. 12 is a diagram illustrating an example of a phase conversion table according to a third exemplary embodiment.

FIGS. 26A to 26D are flowcharts illustrating processing according to the seventh exemplary embodiment.

FIGS. 28A and 28B are schematic views illustrating an example of a specular reflection conversion table and a gloss image clarity conversion table.

FIGS. 30A to 30M are schematic views illustrating an example of illumination images according to the seventh exemplary embodiment.

DESCRIPTION OF THE EMBODIMENTS

Exemplary embodiments for implementing the present invention will be described with reference to the drawings. However, components and elements that will be described in these exemplary embodiments are merely cited as an example, and are not intended to limit the scope of the present invention thereto.

Figure 14:
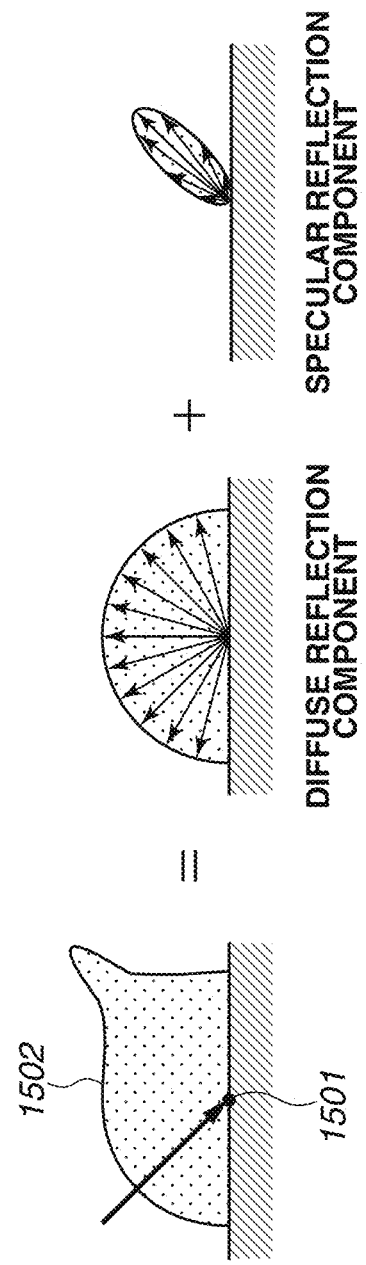
FIG. 14 is a schematic view illustrating a structure of reflected light in a reflection model.

A reflection characteristic of an object will be described. FIG. 14 is a schematic view illustrating the reflection characteristic of the object. A curved line 1502 represents the reflection characteristic of the object when the object is irradiated with light from a direction indicated by an arrow toward a point 1501. A length of a straight line segment connecting the point 1501 and a point on the curved line 1502 represents an intensity of reflected light reflected from the point 1501 in a direction toward the point on the curved line 1502. The light reflected on a surface of the object can be divided into a diffuse reflection component and a specular reflection component. The diffuse reflection component refers to a component generated by a diffuse reflection of incident light inside a measurement surface, and is observed with an even intensity in every direction. On the other hand, the specular reflection component refers to a component indicating a glossy appearance that is generated by a specular reflection of the incident light on a top of the measurement surface, and is observed with an uneven intensity that is high in a specific direction. Hereinafter, a reflection direction where the intensity of the specular reflection component is maximized will be referred to as a maximum reflection direction. The intensity of the specular reflection component exhibits a distribution in which a symmetry center is located at the maximum reflection direction.

Figure 1A:
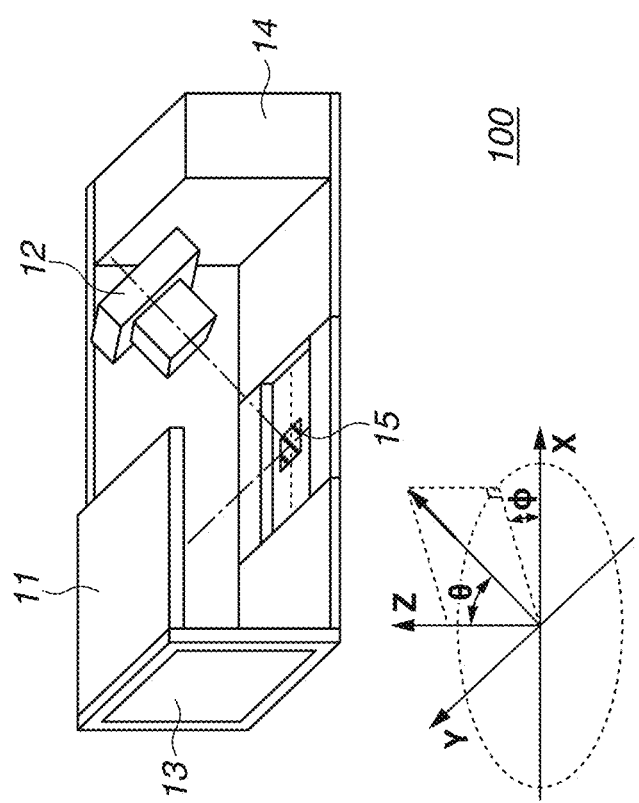
FIG. 1A is a schematic view illustrating an external appearance of a measurement apparatus.
Figure 1B:
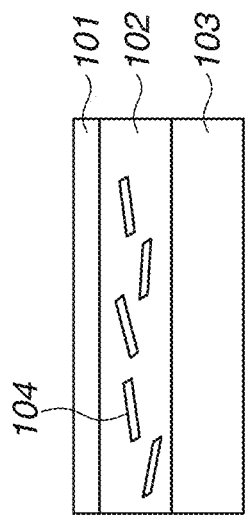
FIG. 1B is a schematic view illustrating a measurement object according to a first exemplary embodiment.

FIG. 1B is a schematic view illustrating a surface structure of a metallic coated plate, which is targeted for measurement by a measurement system according to a first exemplary embodiment. A surface of this coated plate includes a transparent coated layer 101, a colored layer 102, and a base material layer 103. The colored layer 102 contains a bright material 104, such as a metallic fragment. Even when the surface of such a coated plate is illuminated from the same direction, the maximum reflection direction thereof changes depending on a position on the coated plate due to an effect of the bright material 104. A two-dimensional distribution of the maximum reflection direction affects a bright appearance of the metallic coated plate, and determines an appearance of the coated plate. In the first exemplary embodiment, a two-dimensional distribution of an index representing the maximum reflection direction is derived with respect to the object set as the measurement target.

Figure 8:
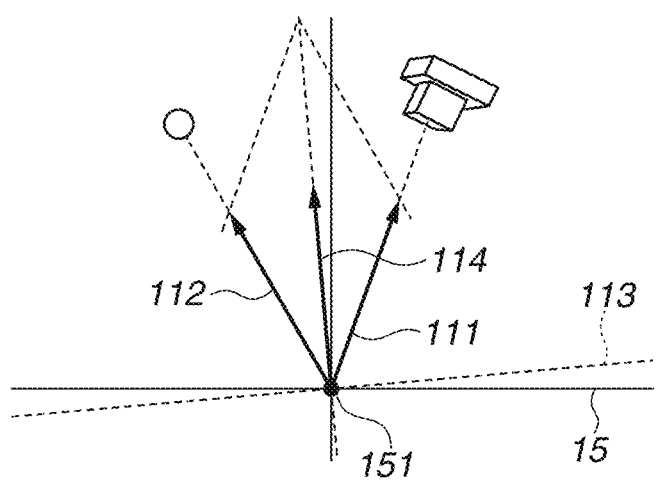
FIG. 8 is a schematic view illustrating an optical normal direction.

Then, an optical normal direction defined in the following manner is used as the index representing the maximum reflection direction. FIG. 8 is a schematic view illustrating the optical normal direction. A vector 112 indicates a direction toward a light source with respect to a measurement point 151 on a measurement object 15. Further, a vector 111 indicates the maximum reflection direction of light from this light source. A virtual surface 113 indicates a surface where the vectors 111 and 112 are in a specular reflection relationship with each other. An optical normal direction 114 is a direction normal to this virtual surface 113, and a direction of a half vector that is a bisection direction between the vector 111 and the vector 112. This definition can also be described in the following manner. That is, the direction of the optical normal direction 114 is the direction of the half vector between the vector 111 indicating a light reception direction and the vector 112 indicating an illumination direction from which the intensity of the reflected light in the above-described light reception direction is maximized as the illumination direction is changed. Hereinafter, the illumination direction where the intensity of the reflected light in the light reception direction is maximized will be referred to as a main illumination direction. The intensity of the reflected light in the light reception direction when the illumination direction is changed exhibits a distribution with a symmetry center located at the main illumination direction.

(Overview of Measurement Apparatus)

FIG. 1A illustrates an external appearance of the measurement system according to the present exemplary embodiment. A measurement system 100 includes an illumination apparatus 11 having a flat plate shape, an imaging apparatus 12, an operation panel 13, and an information processing apparatus 14. In the measurement system 100 in the present exemplary embodiment, the imaging apparatus 12 images the measurement object 15 illuminated by the illumination apparatus 11 based on a user operation with use of the operation panel 13. The information processing apparatus 14 derives a two-dimensional distribution of the optical normal direction on the measurement object 15 based on a captured image acquired from the imaging by the imaging apparatus 12. In the following description, directions of X, Y, and Z coordinates, and directions of a zenith angle θ and an azimuth angle φ with respect to the illumination direction, the light reception direction, the normal direction, and like are defined as illustrated in FIG. 1A. An origin of the X, Y, and Z coordinates is set to an intersection point between an optical axis of the imaging apparatus 12 and the surface of the measurement object 15, and an XY plane is set to the surface of the measurement object 15.

The illumination apparatus 11 illuminates the measurement object 15 using a plurality of point light sources arrayed on a surface of the illumination apparatus 11. Each of the point light sources can be independently controlled in terms of a luminance (a light intensity) thereof, and is not only turned on and off but also emits light with multi-tone intensities corresponding to illumination images, which will be described below. In the present exemplary embodiment, the illumination apparatus 11 includes a flat panel display set opposite from the measurement object 15, and each of a plurality of pixels on this display functions as the point light source. The pixels on the display of illumination apparatus 11 may be referred to as source pixels. A surface of the display of the illumination apparatus 11 is set in parallel with the measurement object 15 while facing toward the measurement object 15. The display may be a monochrome display.

Figure 9:
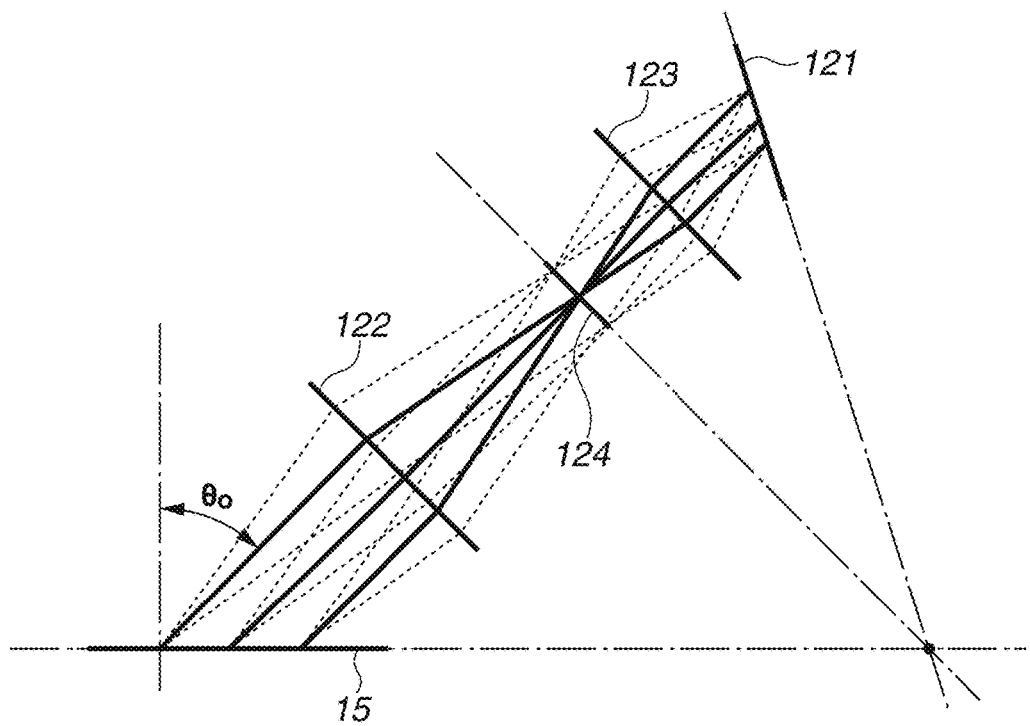
FIG. 9 is a schematic view illustrating an optical system of an imaging apparatus according to the first exemplary embodiment.

The imaging apparatus 12 is a digital camera including a lens that converges light, and a sensor that receives light. The lens is a bilateral telecentric lens, and an optical axis direction of the lens, which relates to the light reception direction, is set at an azimuth angle φo of 0 degrees and a zenith angle θo of 45 degrees. The lens forms an image of the measurement object 15 on a sensor surface. This means that each of a plurality of pixels in the image generated by the sensor is associated with one point on the surface of the measurement object 15. The pixels in the image generated by the sensor may be referred to as image pixels. Since the optical axis of the lens is oblique with respect to the surface of the measurement object 15, the sensor surface and the lens are set at positions that satisfy the known Scheimpflug principle. FIG. 9 is a schematic view illustrating an optical system of the imaging apparatus 12 including the lens and the sensor, which are set at the positions that satisfy the Scheimpflug principle. Light reflected on the surface of the measurement object 15 passes through a principal surface 122 of a first lens, an aperture 124, and a principal surface 123 of a second lens in this order, and is imaged on a sensor surface 121. The sensor is a two-dimensional sensor, such as a charge coupled device (CCD) sensor and a complementary metal-oxide semiconductor (CMOS) sensor including a light-receiving element. Each light-receiving element of the sensor converts an intensity of the received light into an electric signal. As a result, the generated image is formed from image pixels each having a pixel value proportional to the intensity of the received light.

The first lens and the second lens form the telecentric lens, whereby a principal ray runs in parallel with the optical axis. Therefore, the light reception direction is kept constant (θo) at all measurement points on the measurement object 15. Assume that the number of tones indicatable by the pixel value in the image generated by the sensor is 10 bits, a size of the sensor is ⅔ inches, and an imaging resolution is 800 dpi. Since the imaging apparatus 12 images the measurement object 15 from the oblique direction, generally, the imaging resolution is different between the X direction and the Y direction. Resolution conversion processing for making the resolution consistent between the X direction and the Y direction may be performed immediately after the imaging, may be performed after image processing that will be described below and before an output of a measurement result, or may be omitted.

In the present exemplary embodiment, a touch panel is employed as the operation panel 13. A user of the measurement system 100 sets various kinds of measurement conditions and issues an instruction to start the measurement via a user interface on the operation panel 13. Further, the operation panel 13 also functions as a display for displaying information, and displays set measurement conditions and a measurement result.

The information processing apparatus 14 controls the illumination apparatus 11 and the imaging apparatus 12 to acquire the captured image of the measurement object 15 based on a user's instruction input via the operation panel 13. Further, the information processing apparatus 14 performs calculation processing that will be described below on the captured image, and calculates the two-dimensional distribution of the optical normal direction. In other words, in the first exemplary embodiment, the information processing apparatus 14 functions as an illumination control unit, an imaging control unit, and an image processing unit. Further, the information processing apparatus 14 outputs a processing progress and a processing result of the calculation processing to the operation panel 13 and/or a not-illustrated external apparatus.

(Overview of Measurement Method)

Now, an overview of a method by which the measurement system 100 according to the first exemplary embodiment measures a reflection characteristic of the measurement object 15 will be described. FIGS. 5A to 5C illustrate a relationship between the light source and the reflected light received by the imaging apparatus 12. A sensor pixel P on a sensor of the imaging apparatus 12 receives light reflected on a position where the measurement point 151 is located on the measurement object 15. Further, suppose that a maximum reflection direction of light with which the measurement object 15 is irradiated on the measurement point 151 from a point light source Ln is a direction toward the sensor pixel P, and the measurement object 15 is a highly specular object like a mirror. In this case, when a luminance of the point light source Ln is modulated sinusoidally as illustrated in FIG. 5B, a luminance value at the sensor pixel P changes as illustrated in FIG. 5C similarly to FIG. 5B.

Figure 6A:
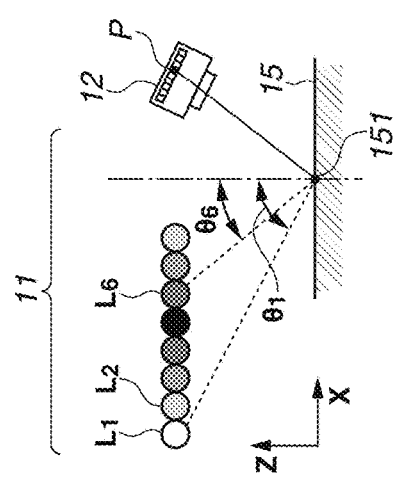
FIGS. 6A, 6B, and 6C are schematic views illustrating an illumination apparatus, and a relationship between modulation information and an illumination luminance of each of point light sources according to the first exemplary embodiment.

The illumination apparatus 11 according to the first exemplary embodiment includes the display where the point light sources are arranged at a plurality of positions as illustrated in FIG. 6A. FIG. 6A is a schematic view illustrating a positional relationship between each of the source pixels on the display of the illumination apparatus 11, which is used as the point light source, and the imaging apparatus 12, and illustrates an XZ cross section of the measurement system 100. FIG. 6A illustrates an example in which eight source pixels are arrayed per row on the display for the purpose of illustration. Each of the point light sources Lj {j: 1, 2, . . . 8} corresponds to the source pixel on the display of the illumination apparatus 11. Each of the point light sources Lj illuminates the measurement point 151 on the measurement object 15 from a different direction θj. Reflected light reflected on the measurement point 151 is received by the sensor pixel P on the imaging apparatus 12. In the case where the measurement object 15 is highly specular, the sensor pixel P mainly receives light with which the measurement object 15 is irradiated from a point light source arranged at a position in the main illumination direction among the light beams from the individual point light sources Lj. Therefore, in the first exemplary embodiment, the measurement system 100 modulates the luminance of each of the point light sources Lj sinusoidally out of phase with one another, thereby identifying, for each of the sensor pixels on the imaging apparatus 12, which point light source is the light source of mainly received light, and deriving the main illumination direction corresponding to each of the sensor pixels. Hereinafter, the point light source arranged at the position in the main illumination direction will be referred to as a main light source.

Figure 6B:
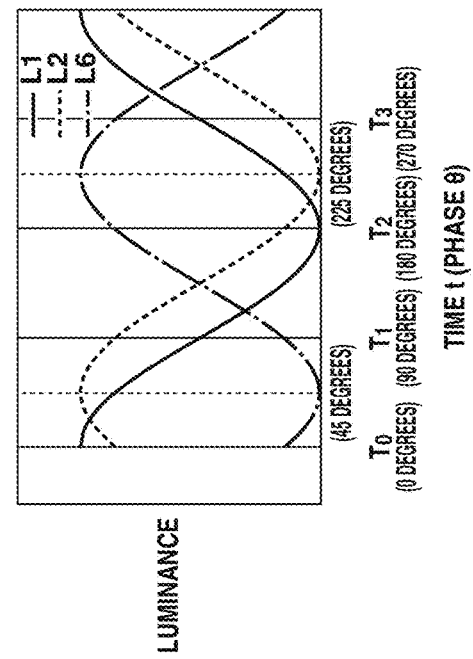
Figure 6C:
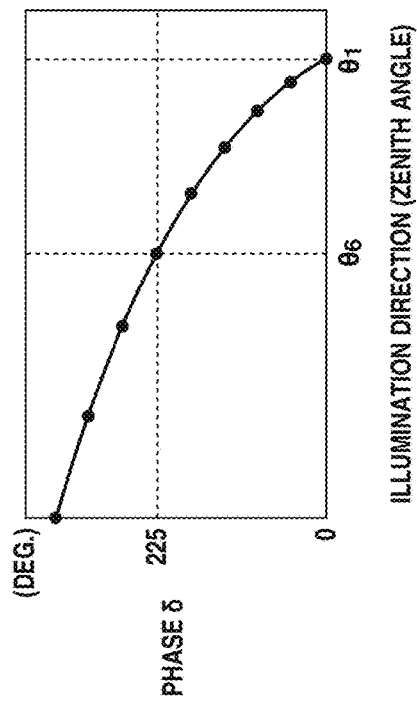
Figure 7:
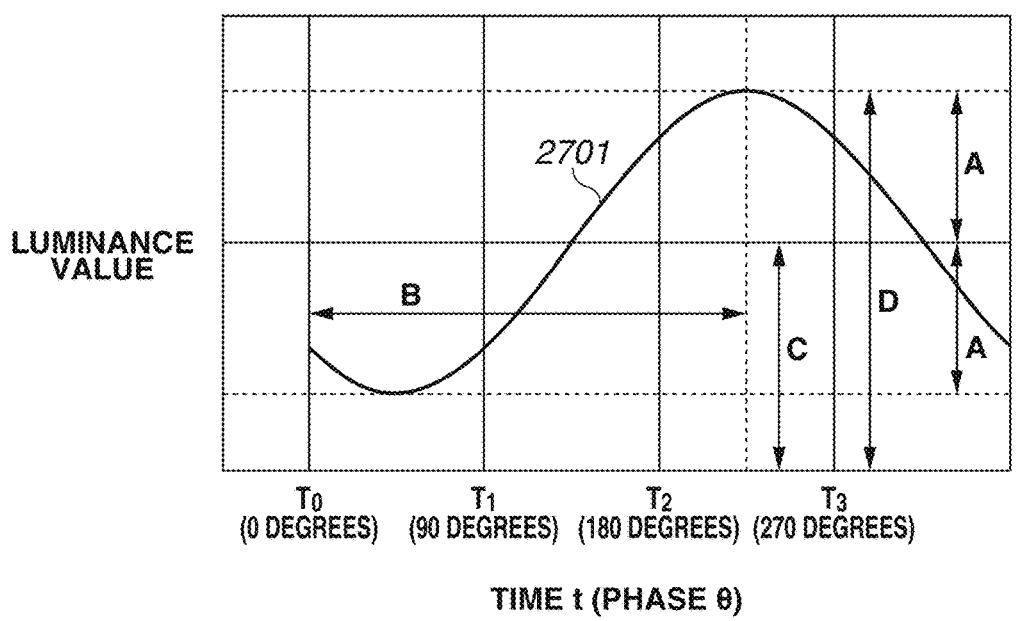
FIG. 7 is a schematic view illustrating a change in a luminance value at a pixel.

FIG. 6B is a schematic view illustrating an example of luminance modulation of each of point light sources L1, L2, and L6. All the point light sources L1, L2, and L6 are modulated sinusoidally, but are out of phase with one another based on a phase of the point light source L1. FIG. 6C illustrates a relationship between the illumination direction (zenith angle) and the phase of each of the point light sources Lj. As illustrated in FIG. 6B, assume that the luminance of the point light source L1 is modulated according to $K1 \cos(\omega t)+K2$ with respect to time t. In other words, the luminance of the point light source L1 is maximized at time t=0. Assume that a phase δ of this sinusoidal wave is 0 degrees. K1 and K2 are constants set according to a luminance range controllable by the illumination apparatus 11. Further, ω is an angular frequency of the modulation. Then, time t is associated with a phase θ calculated from $\theta=\omega t$. Similarly, a phase δ of the point light source L2 is 45 degrees, and the luminance thereof is modulated according to $K1 \cos(\theta-45)+K2$. In other words, the luminance thereof is maximized at a time corresponding to θ=45 degrees. A phase δ of the point light source L6 is 225 degrees, and the luminance thereof is modulated according to K1 cos(θ−225)+K2. In other words, the luminance thereof is maximized at a time corresponding to θ=225 degrees. In other words, each of the point light sources Lj is modulated in such a manner that the luminance thereof is maximized at the time corresponding to the phase θ that becomes θ=δ based on the set phase δ. Suppose that the imaging apparatus 12 captures a moving image of the measurement object 15 while the luminance of each of the point light sources Lj is modulated sinusoidally out of phase with one another in this manner. In this case, the luminance value at the sensor pixel P on the sensor of the imaging apparatus 12 changes, for example, as illustrated in FIG. 7. In FIG. 7, a vertical axis represents the luminance value at the sensor pixel P, and a horizontal axis represents an imaging time, which is indicated in association with the phase θ of the illumination apparatus 11. As described above, the sensor pixel P mainly receives light from the main light source. Therefore, a phase B (a value of θ corresponding to a time period from when the illumination is started until when the luminance value is maximized) matches the phase δ of the main light source for the measurement point 151. In other words, the main illumination direction can be derived from the phase B at each of the sensor pixels. In the example illustrated in FIG. 7, the phase B is 225 degrees, which reveals that the main light source and the main illumination direction for the measurement point 151 are the point light source L6 and θ6, respectively.

In a case where the measurement object 15 is less specular, the sensor pixel P also receives the reflected light from each of the point light sources other than the main light source. However, as described above, the intensity of the reflected light in the light reception direction exhibits the distribution in which the symmetry center is located at the main illumination direction. Therefore, assuming that δm represents a phase of a main light source Lm, almost equal intensities of reflected lights are derived from a point light source Lm+1 having a phase δm+δ1 and a point light source Lm−1 having a phase δm−δ1, which are located adjacent to the main light source Lm. Similarly, almost equal intensities of reflected light are derived from an i-th point light source Lm+i (a phase δm+δi) from the main light source Lm subsequent to the main light source Lm, and an i-th point light source Lm−i (a phase δm−δi) from the main light source Lm prior to the main light source Lm. In this case, a luminance value I at the sensor pixel P is expressed by the following equation (1).

$$I = A0\cos(\theta - \delta m) + C0 + \sum \{Ai\cos(\theta - \delta m + \delta i) + Ci\} + \quad (1)$$
$$\sum Ai\cos(\theta - \delta m - \delta i) + Ci$$
$$= A0\cos(\theta - \delta m) + C0 +$$
$$\{\sum Ai\{\cos(\theta - \delta m)\cos(\delta i) - \sin(\theta - \delta m)\sin(\delta i)\} + Ci\} +$$
$$\{\sum Ai\{\cos(\theta - \delta m)\cos(\delta i) + \sin(\theta - \delta m)\sin(\delta i)\} + Ci\}$$
$$= A0\cos(\theta - \delta m) + 2\cos(\theta - \delta m)\sum Ai\cos(\delta i) + C0 + 2\sum Ci$$
$$= \{A0 + 2\sum Ai\cos(\delta i)\}\cos(\theta - \delta m) + C0 + 2\sum Ci$$

In this equation (1), Σ indicates that a sum with respect to an index i is calculated. A0 and C0 are constants representing a reflectance with respect to the light from the main light source Lm (the main illumination direction). Ai and Ci are constants representing a reflectance with respect to the light from the i-th point light source Lm+1 or Lm−1 from the main light source Lm. As indicated in the equation (1), the value of θ where the luminance value I at the sensor pixel P is maximized (the phase B) is the phase δm. Therefore, even in the case where the measurement object 15 is less specular, the phase B matches the phase δm of the main light source Lm. Further, in the first exemplary embodiment, a gloss intensity is also measured at each of the measurement points on the measurement object 15. The gloss intensity refers to a reflection intensity in the maximum reflection direction, and, for example, specular glossiness as defined by Japanese Industrial Standards (JIS) Z8741. The gloss intensity G is derived in the following manner. First, a maximum luminance value D in the change in the luminance value at the sensor pixel P illustrated in FIG. 7 is calculated as maximum luminance information. A correspondence relationship between the maximum luminance information and the gloss intensity is held in advance by measuring an object having a known gloss intensity. The gloss intensity at each of the measurement points on the measurement object 15 is acquired by referring to this correspondence relationship from the above-described maximum luminance information.

(Configuration of Information Processing Apparatus)

Figure 2A:
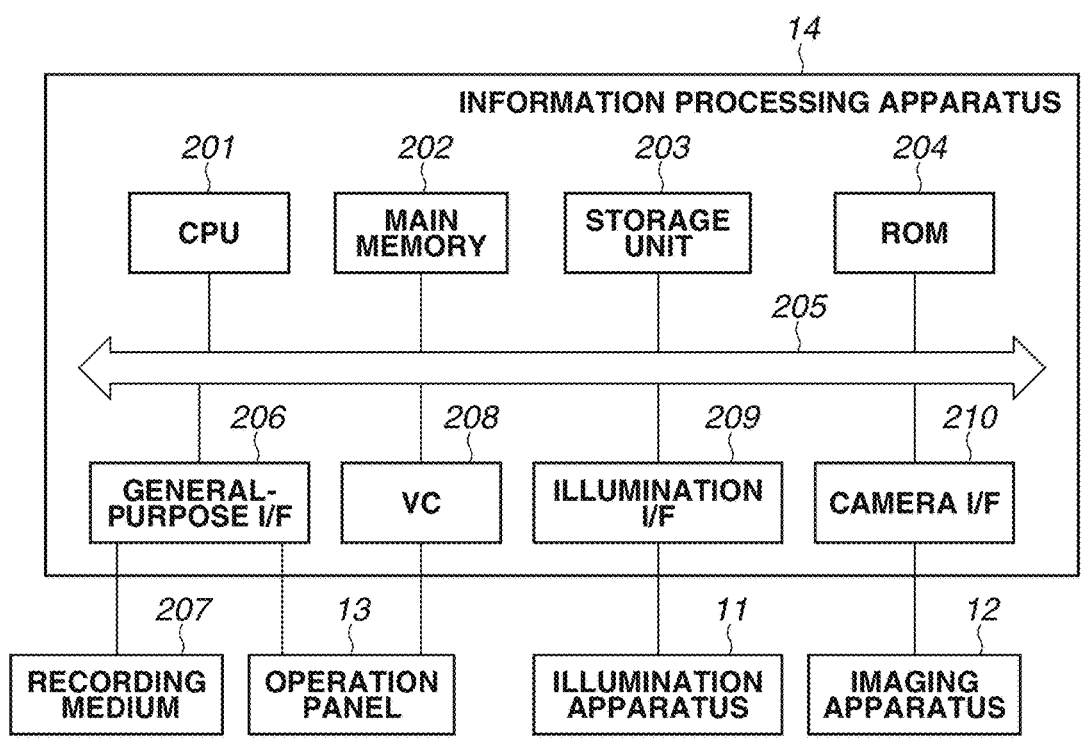

A configuration of the information processing apparatus 14 that controls the illumination apparatus 11 and the imaging apparatus 12 and performs the image processing will be described. FIG. 2A illustrates a hardware configuration of the information processing apparatus 14. A microprocessor (central processing unit (CPU)) 201 uses a main memory 202, such as a random access memory (RAM), as a work memory. The CPU 201 executes a program stored in a storage unit 203, such as a hard disk drive (HDD) or a solid state drive (SSD), or a read only memory (ROM) 204, and controls the illumination apparatus 11 and the imaging apparatus 12 via a system bus 205. A program and various kinds of data for realizing the measurement are stored in the storage unit 203 and/or the ROM 204. The operation panel 13, a recording medium (a recoding medium readable by a computer) 207, such as a universal serial bus (USB) memory or a memory card, and the like are connected to a general-purpose interface (I/F) 206, such as a USB. The operation panel 13 is also connected to a video card (VC) 208. A user interface (UI) and information indicating a processing progress and a processing result of the image processing that will be described below are displayed on the operation panel 13 by the CPU 201. The illumination apparatus 11 is connected to the system bus 205 via an illumination interface (I/F) 209, such as a video card. The imaging apparatus 12 is connected to the system bus 205 via a camera interface (I/F) 210, such as a USB or a camera link. The CPU 201, for example, loads an application program (AP) and various kinds of data stored in the ROM 204, the storage unit 203, or the recording medium 207 into a predetermined area in the main memory 202 according to a user's instruction input via the operation panel 13. The CPU 201 executes the AP and displays the UI on the operation panel 13 according to the AP. The CPU 201 images the surface of the measurement object 15 by controlling the illumination apparatus 11 and the imaging apparatus 12 according to a user's instruction input with use of the UI. The CPU 201 stores captured image data into the main memory 202 or the storage unit 203. The CPU 201 performs predetermined calculation processing on the captured image data stored in the main memory 202 according to the AP. The CPU 201 displays a result of the calculation processing on the operation panel 13 and/or stores this result into the storage unit 203 or the recording medium 207 according to a user's instruction. The CPU 201 can also transmit or receive any of the program, the data, the result of the calculation processing, and intermediate processing data between the information processing apparatus 14 and a computer apparatus or a server apparatus in a wired or wireless network via a not-illustrated network I/F connected to the system bus 205.

(Functional Configuration of Information Processing Apparatus 14)

FIG. 2B is a block diagram illustrating a functional configuration of the information processing apparatus 14 according to the present exemplary embodiment. A detailed functional configuration of the information processing apparatus 14 will be described with reference to FIG. 2B. The information processing apparatus 14 includes a device control unit 901, a data storage unit 902, and a captured image correction unit 903. The device control unit 901 transfers the illumination images to the illumination apparatus 11, and causes the illumination images to be displayed on the display of the illumination apparatus 11. The device control unit 901 causes the imaging apparatus 12 to image the measurement object 15 illuminated based on the illumination images, and stores captured images acquired from the imaging apparatus 12 into the data storage unit 902. The captured image correction unit 903 carries out a predetermined tone correction on the captured images stored in the data storage unit 902.

A phase information calculation unit 904 acquires a phase information distribution based on the corrected images corrected by the captured image correction unit 903. The phase information distribution is an image storing therein the phase B of the change in the luminance value at each of the sensor pixels. The phase B is the information for identifying which point light source (which source pixel on the display) is the main light source. An optical normal direction calculation unit 905 acquires the two-dimensional distribution of the optical normal direction on the measurement object 15 based on the phase information distribution acquired by the phase information calculation unit 904.

In the first exemplary embodiment, the reflection intensity in the direction where the intensity of the reflected light is maximized is calculated as the gloss intensity. A maximum luminance information calculation unit 906 acquires a maximum luminance information distribution based on the corrected images corrected by the captured image correction unit 903. The maximum luminance information distribution is an image storing therein the maximum luminance value D in the change in the luminance value at each of the sensor pixels. A gloss intensity calculation unit 907 acquires a two-dimensional distribution of the gloss intensity based on the maximum luminance information distribution acquired by the maximum luminance information calculation unit 906.

Further, the information processing apparatus 14 includes an optical normal direction image generation unit 908, a normal direction density distribution calculation unit 909, and a brightness information calculation unit 910. The optical normal direction image generation unit 908 generates an optical normal direction image based on the two-dimensional distribution of the optical normal direction that is acquired by the optical normal direction calculation unit 905, and the two-dimensional distribution of the gloss intensity that is acquired by the gloss intensity calculation unit 907. The normal direction density distribution calculation unit 909 acquires a normal direction density distribution based on the two-dimensional distribution of the optical normal direction that is acquired by the optical normal direction calculation unit 905, and the two-dimensional distribution of the gloss intensity that is acquired by the gloss intensity calculation unit 907.

The brightness information calculation unit 910 acquires brightness information of the measurement object 15 based on the two-dimensional distribution of the optical normal direction that is acquired by the optical normal direction calculation unit 905, and the two-dimensional distribution of the gloss intensity that is acquired by the gloss intensity calculation unit 907. The brightness information refers to information correlated to a bright appearance (a metallic appearance) of the measurement object 15. The bright appearance refers to a visual texture due to a change in a position and a size of a luminescent point according to an observation angle. In the present exemplary embodiment, information regarding the size of the luminescent point and a dispersion of luminescent points is formed as the brightness information.

An output unit 911 outputs the two-dimensional distribution of the optical normal direction that is acquired by the optical normal direction calculation unit 905, and the two-dimensional distribution of the gloss intensity that is acquired by the gloss intensity calculation unit 907. The output unit 911 outputs the optical normal direction image generated by the optical normal direction image generation unit 908, the normal direction density distribution generated by the normal direction density distribution calculation unit 909, and the brightness information acquired by the brightness information calculation unit 910. The output unit 911 outputs the captured images corrected by the captured image correction unit 903.

(Regarding Control of Illumination Apparatus 11)

The illumination images that the illumination apparatus 11 is caused to display will be described. Each of the point light sources (the source pixels) on the display irradiates the measurement object 15 with the light modulated sinusoidally out of phase with one another as described above. The information processing apparatus 14 uses the phase corresponding to each of the point light sources as identification information of each of the point light sources. When the imaging apparatus 12 measures the measurement object 15 while each of the point light sources is modulated sinusoidally, the luminance value changes sinusoidally at each of the image pixels in the images generated by the imaging apparatus 12, similarly to the point light source. The main light source and the main illumination direction for each of the measurement points on the measurement object 15 are identified based on the phase of the sinusoidal wave representing the change in the luminance value at each of the sensor pixels. The phase of the sinusoidal wave can be identified as long as there are at least three luminance values. In the first exemplary embodiment, first, the imaging apparatus 12 carries out the imaging four times while the luminance of each of the point light sources is modulated sinusoidally out of phase with one another according to the position of the point light source in the X direction, by which the position of the main light source in the X direction is identified. Similarly, the imaging apparatus 12 carries out the imaging four times while the luminance of each of the point light sources is modulated sinusoidally out of phase with one another according to the position of the point light source in the Y direction, by which the position of the main light source in the Y direction is identified. FIGS. 4A to 4I are diagrams for explaining the illumination images. FIG. 4A illustrates the display, and quadrilaterals represent the source pixels. FIGS. 4B to 4E illustrate the illumination images for identifying the position of the point light source in the X direction, and FIGS. 4F to 4I illustrate the illumination images for identifying the position of the point light source in the Y direction. The information processing apparatus 14 sequentially transmits the illumination images illustrated in FIGS. 4B to 4I to the illumination apparatus 11. The illumination apparatus 11 controls the luminance value at each of the source pixels on the display based on the received illumination images. The information processing apparatus 14 modulates each of the source pixels (the point light sources) on the display of the illumination apparatus 11 by switching the illumination images. The luminance value L at each of the source pixels on the display is expressed by the following equation (2).

$$L(Xd,Yd,\Delta i)=K1\times\cos(\Delta i-\delta(Xd,Yd))+K2 \quad (2)$$

In this equation (2), Xd and Yd are pixel numbers representing the positions of the source pixels on the display of the illumination apparatus 11, in the X-axis direction and the Y-axis direction respectively. $\Delta i$ represents modulation information, K1 and K2 are constants, and $\delta$ represents a phase distribution function indicating the phase at each of the source pixels. The constants K1 and K2 are parameters of a contrast and an average luminance in an illumination pattern, respectively. In a case where the pixel value at each of the source pixels in the illumination image is 8 bits (256 tones), for example, the constants K1 and K2 are 127. The phase distribution function $\delta$ is provided as indicated by the following equations (3) and (4).

$$\delta(Xd,Yd)=K3\times Xd \quad (3)$$

$$\delta(Xd,Yd)=K4\times Yd \quad (4)$$

In these equations (3) and (4), K3 and K4 are constants representing a phase difference between adjacent point light sources. The phase distribution function $\delta$ expressed by the equation (3) corresponds to the illumination images illustrated in FIGS. 4B to 4E, and means that the phase is determined according to the position of the source pixel (the point light source) in the X direction. Similarly, the phase distribution function $\delta$ expressed by the equation (4) corresponds to the illumination images illustrated in FIGS. 4F to 4I, and means that the phase is determined according to the position of the source pixel (the point light source) in the Y direction. The modulation information $\Delta i$ in the equation (2) indicates a phase corresponding to a sampling time of the luminance modulation, and the value of the index i indicates a sampling number of the luminance modulation. In a case where the number of samplings for the luminance (the number of illumination images) is n, values from 1 to n are assigned to i. In the present exemplary embodiment, the number of samplings is n=4, and $\Delta i$ is assumed to be ($\Delta 1$, $\Delta 2$, $\Delta 3$, $\Delta 4$)=(0 degrees, 90 degrees, 180 degrees, 270 degrees). The sampling numbers of the illumination images illustrated in FIGS. 4B to 4E and FIGS. 4F to 4I are 1 to 4, respectively.

(Measurement Procedure)

FIGS. 3A and 3B are flowcharts illustrating a measurement procedure performed by the information processing apparatus 14 according to the present exemplary embodiment. The CPU 201 included in the information processing apparatus 14 reads out and executes a program for performing the flowcharts that will be described below, by which each step is realized.

First, in step S301, the device control unit 901 sequentially transfers each of the illumination images illustrated in FIGS. 4B to 4I to the illumination apparatus 11, and causes the illumination apparatus 11 to display them. When the illumination apparatus 11 illuminates the measurement object 15, the imaging apparatus 12 is caused to image the measurement object 15. As a result, eight captured images can be acquired. Hereinafter, the illumination images illustrated in FIGS. 4B to 4E will be referred to as a first group, and the illumination images illustrated in FIGS. 4F to 4I will be referred to as a second group. The data storage unit 902 stores the acquired captured images. The captured image correction unit 903 carries out the predetermined tone correction on each of the captured images.

In step S302, the phase information calculation unit 904 acquires the phase information distribution for each of the first group and the second group based on the corrected captured images acquired in step S301. First, the phase information calculation unit 904 calculates the phase B for each of the image pixels in the captured images based on the four captured images which are acquired by imaging the measurement object 15 while the measurement object 15 is illuminated with the illumination images in the first group, thereby acquiring the phase information distribution for the first group. FIG. 7 illustrates an example of the change in the luminance value at a processing target pixel in the captured images. A horizontal axis represents the modulation information corresponding to the sampling time, and a vertical axis represents the luminance value in the captured image when the measurement object 15 is illuminated with the illumination image corresponding to the modulation information. The phase information calculation unit 904 plots the luminance values at the processing target pixel in the four captured images. A result of this measurement changes sinusoidally, so that the phase information calculation unit 904 fits the four plotted points to the sinusoidal wave expressed by the equation (2), thereby acquiring a curved line 2701. Then, the phase information calculation unit 904 calculates the phase B of the fitted sinusoidal wave as the phase information. Now, the phase B is an estimated value of the phase corresponding to the time when the luminance value is maximized. In the first exemplary embodiment, the following equations (5) to (8) are used as a method for calculating the phase B.

When ss and sc are 0≤ss and 0≤sc, respectively, $$B=\arctan(ss/sc) \quad (5)$$

When ss and sc are 0≤ss and sc<0, respectively, $$B=\arctan(ss/sc)+180° \quad (6)$$

When ss and sc are ss<0 and sc<0, respectively, $$B=\arctan(ss/sc)+180° \quad (7)$$

When ss and sc are ss<0 and 0≤sc, respectively, $$B=\arctan(ss/sc)+360° \quad (8)$$

In the equations (5) to (8), values of ss and sc are acquired according to the following equations (9) and (10).

$$ss=\Sigma(Ii\times\sin(\Delta i)) \quad (9)$$

$$sc=\Sigma(Ii\times\cos(\Delta i)) \quad (10)$$

Figure 24:
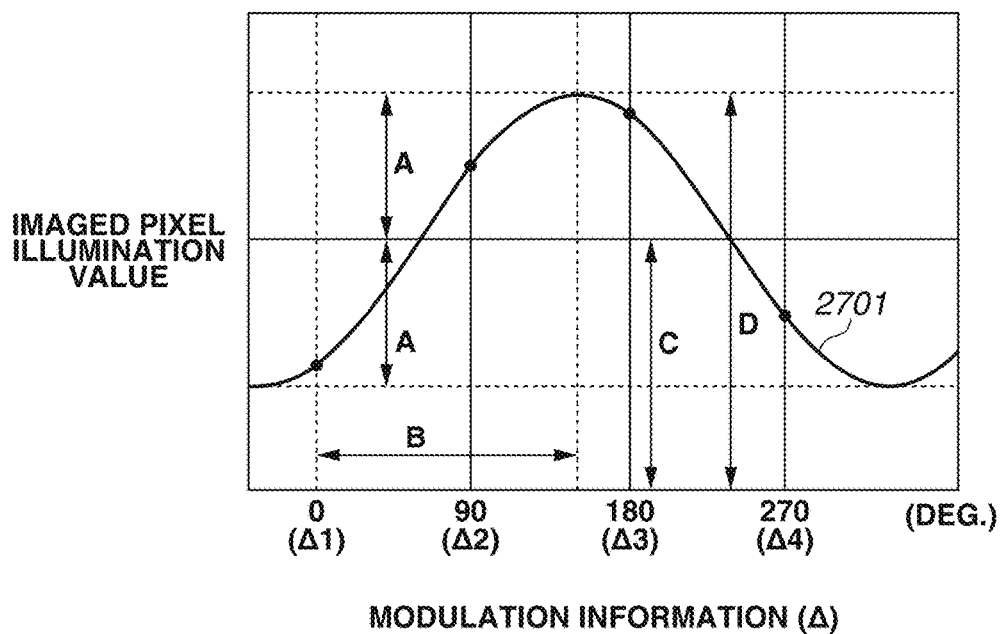
FIG. 24 is a schematic view illustrating amplitude information, phase information, and bias information with respect to the change in the luminance at the pixel.

In these equations (9) and (10), $\Sigma$ indicates that a sum with respect to the index i is calculated. The method for calculating the phase B is not limited to this method. The change in the luminance value at each of the image pixels in the captured images in each of the groups is synchronized with the change in the luminance value at one of the source pixels (the point light sources) in the illumination images, which is expressed by the equation (2). Therefore, the phase B may be acquired by finding a sinusoidal wave in synchronization with the fitted sinusoidal wave illustrated in FIG. 24 (the curved line 2701) from the plurality of sinusoidal waves out of phase with one another that are expressed by the equation (2), and setting the phase of this sinusoidal wave as the phase B.

The phase B calculated by the phase information calculation unit 904 matches the phase of the main light source. Further, the phase of each of the illumination images in the first group is determined according to the position of the source pixel (the point light source) in the X direction. Therefore, a pixel number $Xd_a$ of the main light source in the X direction is acquired from a value $B_{a1}$ of the phase B calculated based on the captured images which are acquired by imaging the measurement object 15 while the measurement object 15 is illuminated with the illumination images in the first group. Details thereof will be described below. Similarly, the phase information calculation unit 904 calculates a value $B_{a2}$ of the phases B for each of the image pixels in the captured images based on the four captured images which are acquired by imaging the measurement object 15 while the measurement object 15 is illuminated with the illumination images in the second group, thereby acquiring the phase information distribution for the second group. A pixel number $Yd_a$ of the main light source in the Y direction is acquired from this phase $B_{a2}$.

In step S303, the optical normal direction calculation unit 905 acquires the two-dimensional distribution of the optical normal direction Nv for each of the image pixels in the captured images. Details thereof will be described below.

In step S304, the maximum luminance information calculation unit 906 calculates the maximum luminance information for each of the image pixels based on the corrected captured images acquired in step S301, thereby acquiring the maximum luminance information distribution. The maximum luminance information is D illustrated in FIG. 7, and is averaged after being calculated for each of the groups of the illumination images. The maximum luminance information calculation unit 906 plots the luminance values at the processing target pixel in the four captured images, and fits these four plotted points to the sinusoidal wave expressed by the equation (2), thereby acquiring the curved line 2701. Then, the maximum luminance information calculation unit 906 calculates the maximum luminance D in the fitted sinusoidal wave as the maximum luminance information. The maximum luminance D is a sum of amplitude information A and bias information C of the fitted curved line 2701. In the first exemplary embodiment, the following equation (11) is used as a method for calculating the amplitude information A.

$$A = \sqrt{ss^2 + sc^2} \qquad (11)$$

In the equation (11), ss and sc are acquired from the above-described equations (9) and (10).

Further, in the first exemplary embodiment, the following equation (12) is used as a method for calculating the bias information C.

$$C = \Sigma Ii \qquad (12)$$

In this equation (12), $\Sigma$ indicates that a sum with respect to the index i is calculated. The maximum luminance information calculation unit 906 calculates the maximum luminance information D with use of an equation (13) from the amplitude information A and the bias information C.

$$D = A + C \qquad (13)$$

Next, in step S305, the gloss intensity calculation unit 907 calculates the gloss intensity G with respect to each of the image pixels in the captured images, and acquires the two-dimensional distribution of the gloss intensity G. The two-dimensional distribution of the gloss intensity G is an image storing therein a value of the gloss intensity G corresponding to each of the image pixels in the captured images. The gloss intensity calculation unit 907 refers to a gloss intensity conversion table in which the maximum luminance information D and the gloss intensity G are associated with each other. FIG. 10 is a diagram illustrating an example of the gloss intensity conversion table. As illustrated in FIG. 10, the gloss intensity conversion table is a lookup table in which a correspondence relationship between the maximum luminance information D and the specular glossiness, which are presented as discrete data, is described. The gloss intensity G corresponding to arbitrary maximum luminance information D is calculated by a known interpolation method. The gloss intensity conversion table is created in advance by measuring a surface having known specular glossiness. The gloss intensity calculation unit 907 derives the gloss intensity G at each of the image pixels by referring to the maximum luminance information D at each of the image pixels.

In step S306, the optical normal direction image generation unit 908 generates the optical normal direction image. The optical normal direction image is a color image formed by adding a color according to the zenith angle θn and the azimuth angle φn of the optical normal direction based on the two-dimensional distribution of the optical normal direction that has been acquired in step S303. Assume that a hue angle h and a color saturation C* of a color at each of a plurality of pixels in the optical normal image are, for example, values acquired with use of the following equations (14) and (15) from θn and φn.

$$h = \varphi n \qquad (14)$$

$$C^* = Kc \times \theta n \qquad (15)$$

In this equation (15), Kc is a constant. The plurality of pixels in the optical normal image may be referred to as optical normal image pixels. In this manner, according to the optical normal direction image in which the azimuth angle φn and the zenith angle θn of the optical normal direction are associated with the hue angle h and the color saturation C*, respectively, the distribution of the optical normal direction can be presented for easy understandability. Assume that a brightness L* is set to 50 or a value of brightness with which the color saturation C* is maximized at each hue in a standard Red-Green-Blue (sRGB) color gamut. The values of these L*, C*, and h are converted into sRGB by a known method, and are converted into a normally-used color image in which values of RGB are stored at each of the pixels. A resolution is converted so that the image has the same resolution between the X direction and the Y direction. In the optical normal direction image, a special color may be allocated to an optical normal image pixel having a gloss intensity of a predetermined value or lower based on the two-dimensional distribution of the gloss intensity G that has been acquired in step S305. For example, a black color is allocated. Alternatively, the brightness L* may be allocated according to the gloss intensity. For example, the brightness L* is set so as to reduce as the gloss intensity reduces. Setting the brightness according to the gloss intensity in this manner facilitates identification of a region less contributive to the appearance of the measurement object 15.

Figure 21:
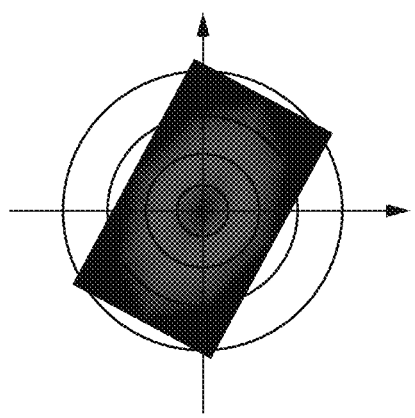
FIG. 21 is a schematic view illustrating a display example of a result of a normal direction density distribution.

In step S307, the normal direction density distribution calculation unit 909 acquires the normal direction density distribution from the two-dimensional distribution of the optical normal direction that has been acquired in step S304. The normal direction density distribution is a histogram of the optical normal direction. The normal direction density distribution is data acquired by dividing the zenith angles θn and the azimuth angles φn of the optical normal directions into a plurality of sections, counting the number of optical normal image pixels corresponding to each of the sections, and calculating a ratio to the total number of image pixels in the captured images acquired by measuring the measurement object 15. According to the normal direction density distribution, a statistical distribution of the optical normal direction of the measurement object 15 can be recognized. FIG. 21 is a schematic view illustrating an example of a display of a result of the normal direction density distribution. A size of a concentric circle corresponds to the zenith angle θn, an angle formed together with a rightward direction of a horizontal axis corresponds to the azimuth angle φn, and lightness/darkness of each point indicates a ratio at which the normal direction corresponding to this point is contained in the measurement surface. When the number of optical normal image pixels corresponding to each of the sections is counted, the count may be processed in such a manner that a pixel having a gloss intensity of a predetermined value or lower is excluded from the count based on the two-dimensional distribution of the gloss intensity G that has been acquired in step S305. Counting the number of optical normal image pixels in this manner can exclude a region less contributive to the appearance of the measurement object 15.

In step S308, the brightness information calculation unit 910 acquires the brightness information based on the two-dimensional distribution of the optical normal direction that has been acquired in step S303. In the present exemplary embodiment, the brightness information is acquired by calculating an average value and a standard deviation of cluster sizes, when a region where the optical normal direction is substantially the same is clustered. The average value of cluster sizes calculated in this processing can be deemed as the size of the luminescent point that indicates the metallic appearance of the measurement object 15. As the standard deviation of cluster sizes increases, luminescent points are more largely dispersed, and therefore it can be said that the measurement object 15 has a stronger metallic appearance depending on an observation angle.

The number of clusters larger in size than a predetermined size may be used as the brightness information. Alternatively, the acquisition of the brightness information may be processed such that a region where the gloss intensity exceeds a predetermined value is clustered based on the two-dimensional distribution of the gloss intensity G that has been acquired in step S305. Referring to such brightness information allows a characteristic of, for example, metallic coating to be managed numerically. For example, a coating quality can be managed by measuring whether one or a plurality of piece(s) of brightness information falls within a predetermined range compared to a reference coated sample.

In step S309, the output unit 911 outputs various kinds of measurement results. Then, the information processing apparatus 14 ends the measurement of the reflection characteristic of the measurement object 15. The output data may include any of the captured images and intermediate data of the above-described processing, including the two-dimensional distributions of the optical normal direction and the gloss intensity, the normal direction distribution image, the normal direction density distribution, and the brightness information.

A procedure for calculating the two-dimensional distribution of the optical normal direction Nv, which is calculated by the optical normal direction calculation unit 905 in step S303, will be described. FIG. 3B is a flowchart illustrating a detailed procedure of step S303. The information processing apparatus 14 reads out and executes a program corresponding to the flowchart illustrated in FIG. 3B, by which the processing by the optical normal direction calculation unit 905 is realized.

In step S801, the optical normal direction calculation unit 905 derives the pixel numbers on the display that serve as the main light source for each of the sensor pixels by referring to the phase distribution calculated by the phase information calculation unit 904. The pixel numbers ($Xd_a$, $Yd_a$) of the main light source can be calculated as indicated by the following equations (16) and (17) based on the above-described equations (3) and (4) from the phase information $B_{a1}$ and $B_{a2}$.

$$Xd_a = B_{a1}/K3 \tag{16}$$

$$Yd_a = B_{a2}/K4 \tag{17}$$

The pixel numbers of the main light source calculated with use of the equations (16) and (17) are not limited to an integer. In other words, with the measurement system 100 according to the present exemplary embodiment, the optical normal direction can be acquired with a higher resolution than an interval between the point light sources of the illumination apparatus 11. Next, in step S802, the optical normal direction calculation unit 905 generates an image storing therein XYZ coordinates of the main light source corresponding to each of the pixels in the captured images as a two-dimensional distribution of the XYZ coordinates of the main light source. The XYZ coordinates (Xill, Yill, Zill) of the main light source in a three-dimensional space can be calculated as indicated by the following equations (18) to (20) from the pixel numbers ($Xd_a$, $Yd_a$), which indicate the pixel position on the display.

$$Xill = Kill_{11} \times Xd_a + Kill_{13} \tag{18}$$

$$Yill = Kill_{22} \times Xd_a + Kill_{23} \tag{19}$$

$$Zill = Kill_{33} \tag{20}$$

In these equations (18) to (20), $Kill_{11}$, $Kill_{13}$, $Kill_{22}$, $Kill_{23}$, and $Kill_{33}$ are constants determined based on the set position and the pixel size of the illumination apparatus 11, and can be acquired in advance.

In step S803, the optical normal direction calculation unit 905 generates an image storing therein XYZ coordinates of the measurement point corresponding to each of the pixels in the captured images as a two-dimensional distribution of the XYZ coordinates of the measurement point. Since the imaging apparatus 12 is focused on the measurement surface of the measurement object 15, the image pixels in the captured images and the points on the top of the measurement surface of the measurement object 15 are associated with each other in a one-on-one manner. The XYZ coordinates (Xsmp, Ysmp, Zsmp) of the measurement point on the measurement object 15 can be calculated as indicated by the following equations (21) to (23) from pixel numbers (Xc, Yc) of the image pixel in the captured images.

$$Xsmp = Kcam_{11} \times Xc + Kcam_{13} \tag{21}$$

$$Ysmp = Kcam_{22} \times Yc + Kcam_{23} \tag{22}$$

$$Zsmp = 0 \tag{23}$$

In these equations (21) and (22), $\text{Kcam}_{11}$, $\text{Kcam}_{13}$, $\text{Kcam}_{22}$, and $\text{Kcam}_{23}$ are constants determined based on the set position and the imaging resolution of the imaging apparatus 12, and can be acquired in advance.

In step S804, the optical normal direction calculation unit 905 acquires a two-dimensional distribution of a directional vector indicating the illumination direction. This is an image storing therein XYZ components of the directional vector indicating the illumination direction corresponding to each of the image pixels in the captured images. The directional vector (Xvi, Yvi, Zvi) indicating the illumination direction corresponding to the main light source can be calculated as indicated by equations (24) to (26) from the respective XYZ coordinates of the main light source and the measurement point.

$$Xvi = \frac{(Xill - Xsmp)}{\text{norm}} \quad (24)$$

$$Xvi = \frac{(Xill - Xsmp)}{\text{norm}} \quad (25)$$

$$Xvi = \frac{(Xill - Xsmp)}{\text{norm}} \quad (26)$$

In the equations (24) to (26), norm is defined by the following equation (27).

$$\text{norm} = \sqrt{(Xill-Xsmp)^2 + (Yill-Ysmp)^2 + (Zill-Zsmp)^2} \quad (27)$$

In step S805, the optical normal direction calculation unit 905 acquires a two-dimensional distribution of a vector indicating the optical normal direction. This is an image storing therein XYZ components of the above-described vector corresponding to each of the pixels in the captured images. The light reception direction in the measurement system 100 according to the present exemplary embodiment is the zenith angle of 45 degrees and the azimuth angle of 0 degrees. Therefore, a directional vector (Xvc, Yvc, Zvc) indicating the light reception direction can be calculated from the following equations (28) to (30).

$$Xvc = 1/\sqrt{2} \quad (28)$$

$$Yvc = 0 \quad (29)$$

$$Zvc = 1/\sqrt{2} \quad (30)$$

The directional vector (Xvn, Yvn, Zvn) indicating the optical normal direction can be calculated as indicated by the following equations (31) to (33) from the respective directional vectors of the illumination direction and the light reception direction.

$$Xvn = \frac{\frac{(Xvi + Xvc)}{2}}{\text{norm}} \quad (31)$$

$$Yvn = \frac{\frac{(Yvi + Yvc)}{2}}{\text{norm}} \quad (32)$$

$$Zvn = \frac{\frac{(Zvi + Zvc)}{2}}{\text{norm}} \quad (33)$$

In the equations (31) to (33), norm is defined by the following equation (34).

$$\text{norm} = \sqrt{\left(\frac{Xvi+Xvc}{2}\right)^2 + \left(\frac{Yvi+Yvc}{2}\right)^2 + \left(\frac{Zvi+Zvc}{2}\right)^2} \quad (34)$$

In step S806, the optical normal direction calculation unit 905 acquires the two-dimensional distribution of the optical normal direction. This is an image storing therein the zenith angle $\theta n$ and the azimuth angle $\varphi n$ of the optical normal direction corresponding to each of the image pixels in the captured images. The zenith angle $\theta n$ and the azimuth angle $\varphi n$ of the optical normal direction can be calculated as indicated by the following equations (35) and (36) from the directional vector (Xvn, Yvn, Zvn) indicating the optical normal direction.

$$\theta n = \arctan(Yvn/Xvn) \quad (35)$$

$$\varphi n = \arctan(\sqrt{Xvn^2 + Yvn^2}/Zvn) \quad (36)$$

By operating in this manner, the optical normal direction calculation unit 905 completes the processing for calculating the optical normal direction corresponding to the maximum reflection direction with respect to all of the measurement points.

As described above, in the present exemplary embodiment, the measurement system 100 illuminates the measurement object 15 by causing the plurality of point light sources of the illumination apparatus 11 to emit light while modulating them sinusoidally out of phase with one another. The imaging apparatus 12 acquires the captured images by imaging the measurement object 15 a plurality of times during one cycle in which each of the point light sources of the illumination apparatus 11 is subjected to the modulation. The maximum reflection direction for each of the image pixels in the captured images is identified by determining from which point light source the each of the sensor pixels mainly receives the reflected light with use of the fact that the luminance value changes with the same phase difference as the phase difference of the main light source therefor. Especially in the above-described exemplary embodiment, the individual point light sources are caused to emit the light at the same time while being modulated so as to produce light amounts out of phase with one another, which can considerably reduce a time period compared to a method that measures the measurement object 15 every time the point light source emits the light while causing the point light sources to emit the light one by one sequentially. Further, the change in the luminance at each of the pixels can be detected by carrying out the imaging only three times at different timings according to the illumination images. As a result, a memory capacity required for storing the captured images and a time period required for the calculations can also be reduced. In the above description, the measurement procedure has been described assuming that the phase corresponding to one cycle is imaged through four times of imaging by way of example. However, in a case where the phase corresponding to one cycle is imaged through three times of imaging, the present method can be achieved by setting the modulation information $\Delta i$ to $(\Delta 1, \Delta 2, \Delta 3) = (0$ degrees, 120 degrees, 240 degrees). However, as the number of times that the illumination image is switched (the number of times that the imaging is carried out) increases, an influence of noise contained in the captured images can be reduced more greatly. Therefore, it is desirable to set the switching of the illumination image (the number of times that the imaging is carried out) in consideration of, for example, accuracy of the measurement by the user.

It is desirable that the display used as the plurality of point light sources is configured to be able to provide a high luminance contrast, which is a ratio between a maximum displayable luminance and a minimum displayable luminance, to keep the luminance stable over time, and to achieve minimal unevenness of the luminance among the individual source pixels in the display, because such a display facilitates the identification of each of the point light sources. It is desirable that the plurality of point light sources is densely arrayed, and each of the plurality of point light sources is caused to emit light while continuously shifting the phase thereof. In the first exemplary embodiment, the display is used for illuminating the measurement object 15. In the case where the display is employed, the resolution of the display is also a density at which the point light sources are arrayed, and affects the measurement accuracy. It is desirable that the size of the display is designed in consideration of allowing the imaging apparatus 12 to receive the specular reflection component (the reflected light from the maximum reflection direction) with respect to all of the measurement points on the measurement surface of the measurement object 15 that the imaging apparatus 12 is supposed to measure.

In the above-described exemplary embodiment, the measurement system 100 has been described as being configured to allocate one cycle of the sinusoidal wave to the eight point light sources by way of example. However, the individual point light sources arrayed in the form of the display do not have to be modulated out of phase with one another so as to correspond to exactly one cycle. For example, as illustrated in FIGS. 23A to 23I, a measurement system 100 may be configured to allocate the phase difference of one cycle to half of the point light sources on the display. In other words, this means that the luminance changes sinusoidally by two cycles in one illumination image, so that a stripe pattern is formed in the illumination image. This case leads to periodic existence of point light sources having the same phase difference on the display. A second exemplary embodiment will be described as a measurement method employed in the case where the point light sources having the same phase difference periodically exist in the X direction or the Y direction on the display in this manner.

Figures 23A, 23B, 23C, 23D, 23E, 23F, 23G, 23H, 23I:
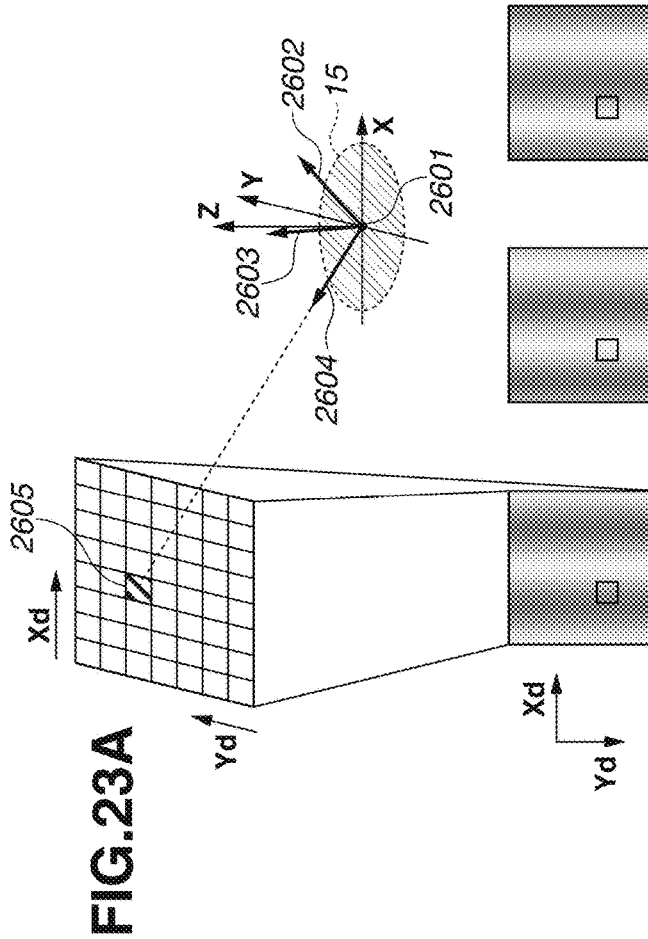
FIGS. 23A to 23I are schematic views illustrating an example of illumination images.

A correction of the phase information B will be described. The value of the phase information B calculated with use of the equations (5) to (8) is within a range from 0 degrees to 360 degrees, and is a remainder resultant from dividing true phase information by 360. Therefore, in a case where δ in the equations (3) and (4) includes a value outside this range, the phase information B is corrected as necessary. Referring to FIG. 23A, a position of a point light source 2605 serving as the main light source for a sensor pixel 2606 (not illustrated), which is the above-described sensor pixel, changes depending on a direction of an optical normal direction 2603. However, the optical normal directions are distributed around the direction normal to the measurement object 15 (the Z direction). Therefore, the point light source 2605 is estimated to be located around the point light source 2605 when the optical normal direction 2603 matches the direction normal to the measurement object 15. Assume that Ps represents a value of the phase δ of the point light source 2605 in this case. The phase information B is corrected so as to fall within a range of ±180 degrees from Ps by adding or subtracting an integral multiple of 360 degrees to or from the original value.

Figure 25:
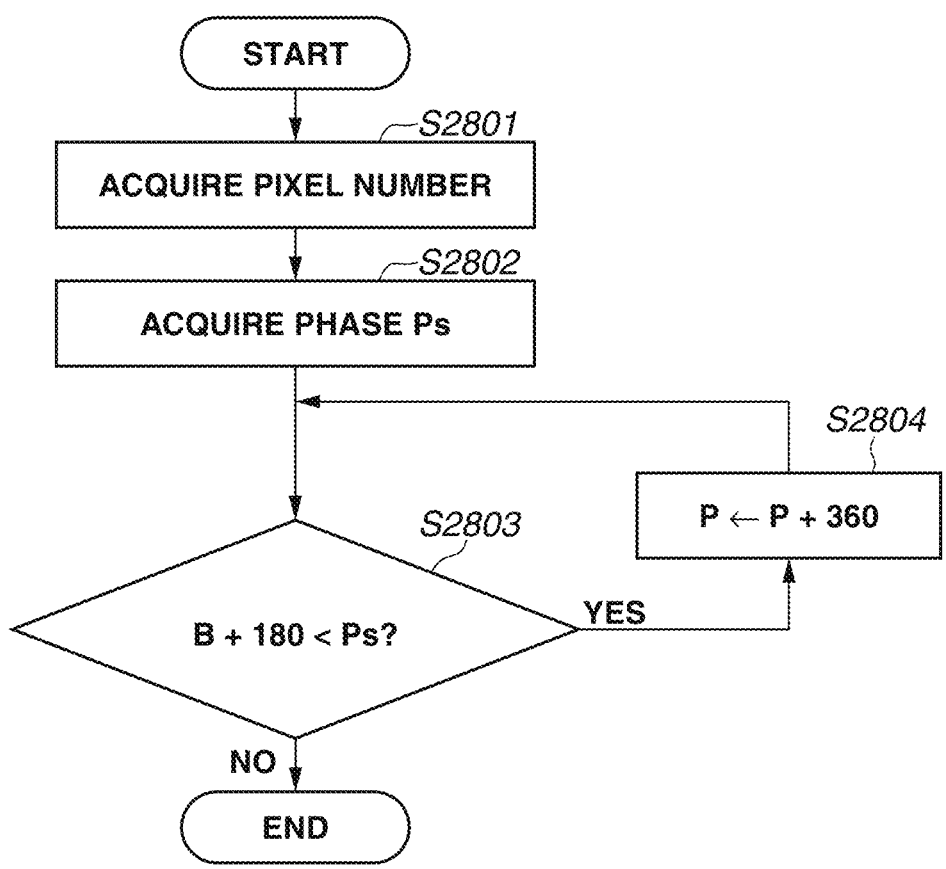
FIG. 25 is a flowchart illustrating a procedure for correcting the phase information.

FIG. 25 is a flowchart illustrating a procedure for correcting the phase information B. In step S2801, the information processing apparatus 14 calculates pixel numbers of the main light source for which the optical normal direction matches the direction normal to the measurement surface of the measurement object 15 with respect to each of the image pixels in the captured images. The pixel numbers ($Xd_b$, $Yd_b$) of the above-described main light source corresponding to the image pixel (Xc, Yc) in the captured images are provided as indicated by the following equations (37) and (38).

$$Xd_b=(Kcam_{11} \times Xc+Kcam_{13}-Kill_{33}-Kill_{13})/Kill_{11} \quad (37)$$

$$Yd_b=(Kcam_{22} \times Yc+Kcam_{23}-Kill_{23})/Kill_{22} \quad (38)$$

In step S2802, the information processing apparatus 14 calculates the phase Ps of the main light source at which the optical normal direction matches the direction normal to the measurement surface of the measurement object 15. Ps is calculated for each of the groups of illumination patterns. Ps to be used in the correction of the phase information B acquired from the images captured with use of the illumination pattern of the first group is calculated by substituting $Xd_b$ calculated in step S2801 into the above-described equation (3). Further, Ps to be used in the correction of the phase information B acquired from the images captured with use of the illumination pattern of the second group is calculated by substituting $Yd_b$ calculated in step S2801 into the above-described equation (4).

Next, in step S2803, the information processing apparatus 14 compares a value of B+180 degrees and the value of Ps calculated in step S2802. If the former is smaller than the latter (YES in step S2803), the processing proceeds to step S2804. Otherwise (NO in step S2803), the information processing apparatus 14 outputs B as the corrected phase information, and then the processing is ended.

In step S2804, the information processing apparatus 14 adds 360 degrees to B. Then, the processing returns to step S2803.

In the first exemplary embodiment, the phase information B is calculated by fitting the change in the luminance at the sensor pixel P on the sensor to the periodic function. In a third exemplary embodiment, a measurement system 100 will be described as employing a method that estimates the phase information B by referring to a conversion table. The third exemplary embodiment is different from the first exemplary embodiment in terms of the processing in step S302 performed by the phase information calculation unit 904 and the processing in step S304 performed by the maximum luminance information calculation unit 906. Similar configurations to the first exemplary embodiment will not be described in detail below.

Figure 13:
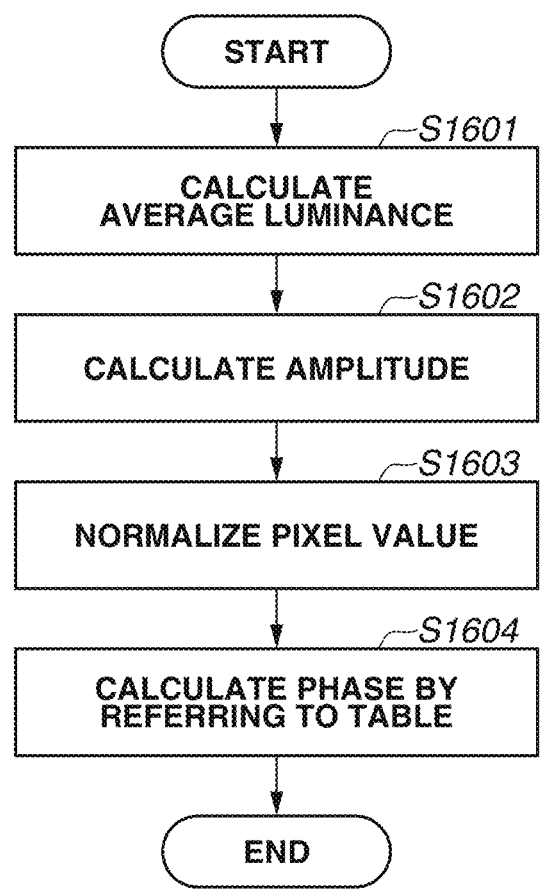
FIG. 13 is a flowchart illustrating details of processing corresponding to step S302, according to the third exemplary embodiment.

Processing in step S302 according to the third exemplary embodiment will be described. FIG. 13 is a flowchart illustrating step S302 according to the third exemplary embodiment. In step S1601, the phase information calculation unit 904 acquires the pixel values Ii at the pixel position (Xc, Yc) in the captured images and calculates an average luminance for each of the groups. The average luminance Iave is calculated with use of the following equation (39).

$$Iave(Xc,Yc)=\Sigma(Ii(Xc,Yc))/n \quad (39)$$

In this equation (39), n represents the number of times that the imaging is carried out with use of each of the illumination groups, and is 4 in the present exemplary embodiment. Σ in the equation (39) indicates that a sum with respect to the index i is calculated.

In step S1602, the phase information calculation unit 904 calculates an amplitude of the change in the luminance at each of the sensor pixels. The amplitude Iamp is, for example, provided as indicated by the following equation (40).

$$Iamp(Xc,Yc)=Max(Max(Ii)-Iave,Iave-Min(Ii)) \quad (40)$$

In this equation (40), Max represents a function for calculating a maximum value of an argument, and Min represents a function for calculating a minimum value of an argument.

In step S1603, the phase information calculation unit 904 normalizes each of the image pixels in the captured image I1 corresponding to the illumination image in which the phase Δ of the modulation information is 0 degrees with use of the average luminance Iave and the amplitude Iamp. A pixel value Icor in the image after the normalization is provided as indicated by the following equation (41).

$$Icor(Xc, Yc) = \frac{(I1(Xc, Yc) - Iave(Xc, Yc))}{Iamp} \quad (41)$$

The pixel value Icor indicates a reflection intensity normalized to have an average of 0 and an amplitude of 1.

In step S1604, the phase information calculation unit 904 calculates the phase information corresponding to the signal Icor acquired with use of the equation (41) by referring to a phase conversion table. The phase conversion table is a table in which the phase information corresponding to the normalized reflection intensity is described, and is stored in the data storage unit 902 in advance. FIG. 12 is a diagram illustrating an example of the phase conversion table. As illustrated in FIG. 12, the phase conversion table is a table holding the phase information corresponding to the normalized reflection intensity, which is presented as discrete data. The phase corresponding to an arbitrary normalized reflection intensity can be calculated with use of a known interpolation method. The phase conversion table is a mathematical table of a cosine function. A correspondence relationship between the phase δ and the normalized reflection intensity Icor described in the phase conversion table satisfies the following equation (42).

$$Icor = \cos(\delta) \quad (42)$$

By this processing, the phase information calculation unit 904 completes the processing for calculating the phase of the change in the luminance at each of the image pixels in the captured images.

In step S304, according to the third exemplary embodiment, the maximum luminance information calculation unit 906 calculates the maximum luminance information D with use of an equation (43) instead of the equation (13) according to the first exemplary embodiment.

$$D(Xc, Yc) = \text{Max}(Ii(Xc, Yc)) \quad (43)$$

As described above, in the third exemplary embodiment, the phase at each of the image pixels is calculated by referring to the phase conversion table instead of fitting the change in the luminance to the trigonometric function based on the measurement results (the luminance values) at all of the image pixels in the captured images. This method can eliminate the necessity of the calculation for fitting the change in the luminance to the trigonometric function, thereby speeding up the phase calculation processing.

In the first exemplary embodiment, the measurement system 100 has been described, by way of example, as employing a method that uses a display configured as a surface light source for the illumination apparatus 11. In a fourth exemplary embodiment, a measurement system 100 will be described as employing a method that uses a line light source where a plurality of point light sources are arrayed in a line. Similar configurations to the first exemplary embodiment will not be described in detail below.

Figure 15:
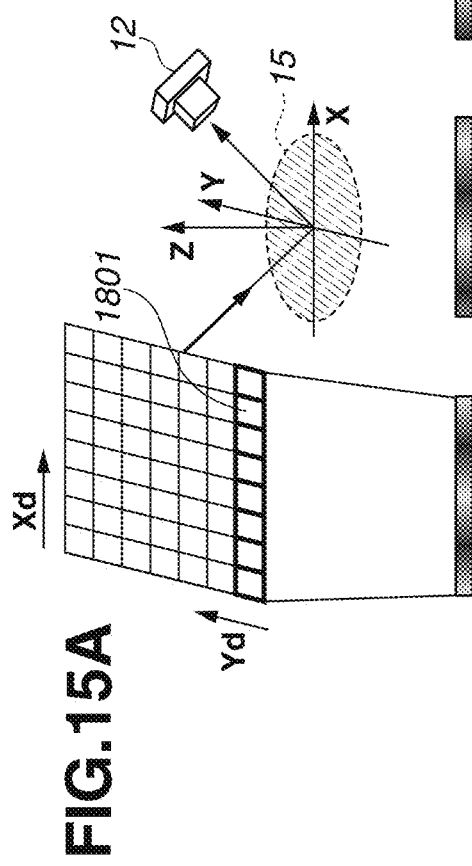
FIGS. 15A to 15E are schematic views illustrating an illumination apparatus according to a fourth exemplary embodiment.

FIGS. 15A to 15E are schematic views for explaining an illumination apparatus according to the fourth exemplary embodiment. As illustrated in FIG. 15A, a line light source 1801 is configured to be movable in the Yd direction. In the fourth exemplary embodiment, the line light source 1801 completes the illumination through multiple operations while being operated to be moved in the Yd direction so as to illuminate the same range as the range illuminated by the illumination apparatus 11 according to the first exemplary embodiment. Alternatively, the line light source 1801 may be configured to be movable in the Xd direction. Each of a plurality of source pixels on the line light source 1801 displays the luminance expressed by the equation (2), similarly to the first exemplary embodiment. As illustrated in FIG. 15A, when the line light source 1801 extending in the Xd direction is driven to scan in the Yd direction, illumination images in a first group are used. A minimum required number of illumination images is 3. FIGS. 15B to 15E illustrate an example in a case where the number of illumination images is 4.

Figure 16:
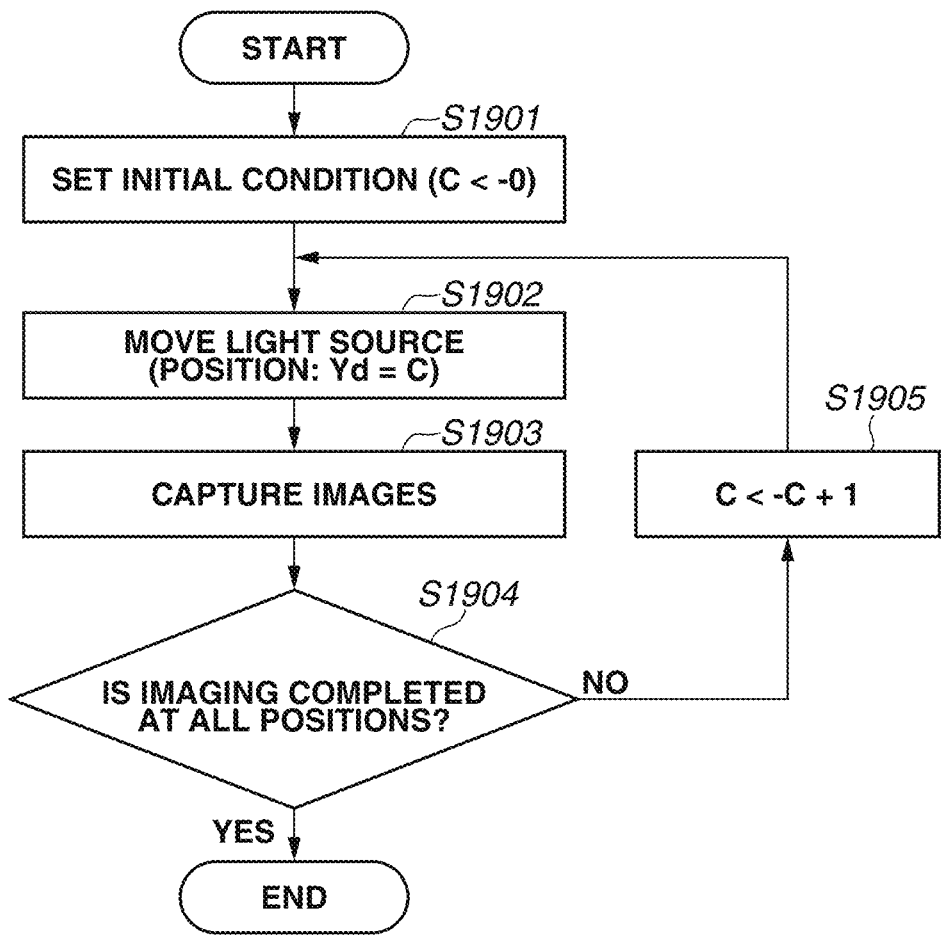
FIG. 16 is a flowchart illustrating details of processing corresponding to step S301, according to the fourth exemplary embodiment.

The fourth exemplary embodiment is different from the first exemplary embodiment in terms of the processing in steps S301 to S303 and the processing in step S304. FIG. 16 is a detailed flowchart of step S301 according to the fourth exemplary embodiment. First, in step S1901, the information processing apparatus 14 sets a constant C, which indicates a scanning position of the line light source 1801 of the illumination apparatus 11, to have a value 0. In step S1902, the information processing apparatus 14 moves the line light source 1801 to a position of Yd=C. In step S1903, the information processing apparatus 14 sequentially transfers the illumination images to the illumination apparatus 11 to cause the illumination apparatus 11 to display them. The information processing apparatus 14 causes the imaging apparatus 12 to image the measurement object 15 when each of the illumination images is displayed. As a result, as many captured images as the number of illumination images are acquired.

In step S1904, the information processing apparatus 14 determines whether the imaging is completed with respect to all of the positions in the Yd direction. If the imaging is completed with respect to all of the scanning positions of the line light source 1801 (YES in step S1904), the processing is ended. Otherwise (NO in step S1904), the processing proceeds to step S1905. In step S1905, the information processing apparatus 14 increments the constant C to set the next scanning position Yd of the line light source 1801. Then, the processing returns to step S1902.

Figure 17:
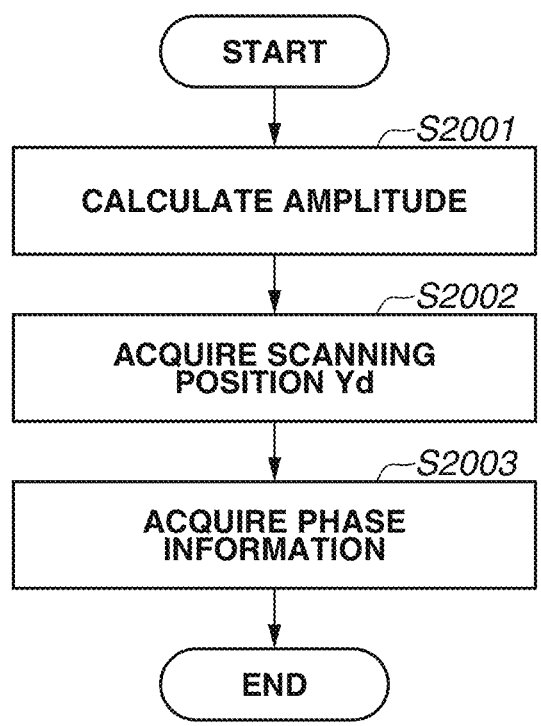
FIG. 17 is a flowchart illustrating a detailed procedure of step S302 according to the fourth exemplary embodiment.

FIG. 17 is a detailed flowchart of step S302 according to the fourth exemplary embodiment. In step S2001, the phase information calculation unit 904 acquires the amplitude information A of the change in the luminance at each of the sensor pixels for each of the scanning positions of the line light source 1801. The amplitude information A is calculated with use of the above-described equations (9), (10), and (11) from the pixel values Ii in the captured images and the modulation information Δi. In step S2002, the phase information calculation unit 904 acquires the scanning position Yd where the amplitude information A is maximized among all of the scanning positions. This scanning position Yd where the amplitude is maximized is acquired for each of the image pixels in the captured images. In step S2003, the phase information calculation unit 904 calculates the phase information for each of the image pixels in the captured images, and acquires the phase distribution for the measurement object 15. The phase information is calculated with use of the above-described equations (5) to (10) from the pixel values Ii in the captured images and the modulation information Δi of when the line light source 1801 is located at the scanning position Yd acquired in step S2002. This phase information corresponds to the phase information B according to the first exemplary embodiment.

Step S303 according to the fourth exemplary embodiment is different from the first exemplary embodiment in terms of the processing in step S801 in the flowchart illustrated in FIG. 3B. In step S801 according to the fourth exemplary embodiment, the optical normal direction calculation unit 905 acquires the pixel number Xd by substituting the phase information B acquired in step S2003 into $B_{a1}$ in the equation (16). The optical normal direction calculation unit 905 uses the scanning position Yd acquired in the above-described step, step S2002 as the pixel number Yd, instead of calculating the pixel number Yd with use of the equation (17).

In processing corresponding to the processing of step S304, the maximum luminance information calculation unit 906 calculates the amplitude information A with use of the above-described equations (9), (10), and (11), from the pixel values Ii in the captured images and the modulation information Δi when the line light source 1801 is located at the scanning position acquired in step S2002. Similarly, the maximum luminance information calculation unit 906 calculates the bias information C with use of the above-described equation (12), from the pixel values Ii in the captured images when the line light source 1801 is located at the scanning position acquired in step S2002.

As described above, the measurement system 100 according to the fourth exemplary embodiment uses the line light source 1801 instead of the surface light source. A line light source is able to achieve a low unevenness in the luminance and provide a highly stable operation. The measurement system can accurately acquire the reflection characteristic, such as the two-dimensional distribution of the optical normal direction, by identifying the maximum reflection intensity while the line light source is driven to scan.

Figure 18:
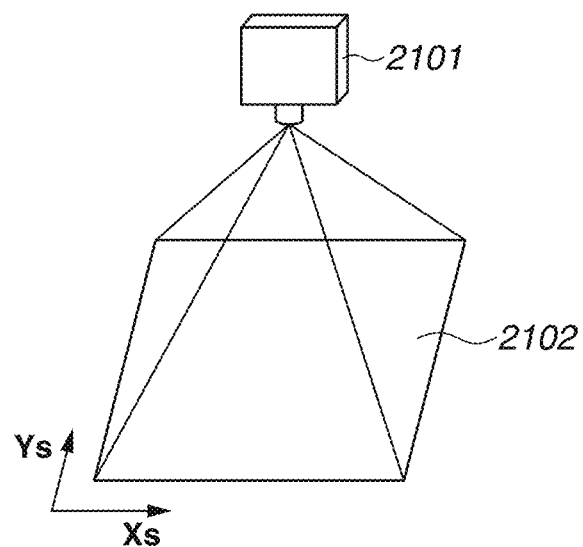
FIG. 18 is a schematic view illustrating an outline of a configuration of an illumination apparatus according to a fifth exemplary embodiment.

In a fifth exemplary embodiment, a measurement system 100 will be described as being configured to use a projector and a screen as the illumination apparatus 11. Similar configurations to the first exemplary embodiment will not be described in detail below. FIG. 18 is a schematic view illustrating the illumination apparatus 11 according to the fifth exemplary embodiment. As illustrated in FIG. 18, the illumination apparatus 11 according to the fifth exemplary embodiment includes a projector 2101, and a screen 2102 of a transparent backside-illumination type. The measurement object 15 (not illustrated in FIG. 18) is disposed below the screen 2102, and is illuminated with light transmitted through the screen 2102. In the present exemplary embodiment, points on a surface of this screen 2102 are used as the point light sources. The points on the surface of the screen 2102 correspond to input pixels in an image input to the projector 2101. The projector 2101 emits light at an arbitrary intermediate level according to a pixel value in the input image. When the pixel value in the image input to the projector 2101 continuously changes in a plane of the image, a luminance level at the point on the surface of the screen 2102 also continuously changes according to this pixel value. The screen 2102 is set in parallel with the surface of the measurement object 15. Assume that (Xs, Ys) represent the point on the surface of the screen 2102 that corresponds to pixel numbers (Xp, Yp) in the image input to the projector 2101. The projector 2101 and the screen 2102 are arranged in such a manner that a straight line is formed on the surface of the screen 2102 by points on the surface of the screen 2102 that correspond to input pixels having the same value as the pixel number Yp in the Y direction of the projector 2101. Respective setup positions of the projector 2101 and the screen 2102 are determined so that a direction along this straight line runs in parallel with the X-axis direction of the measurement apparatus. Similarly, the projector 2101 and the screen 2102 are arranged in such a manner that a straight line is formed on the surface of the screen 2102 by points on the surface of the screen 2102 that correspond to input pixels having the same value as the pixel number Xp in the X direction of the projector 2101. The respective setup positions of the projector 2101 and the screen 2102 are determined so that a direction along this straight line runs in parallel with the Y-axis direction of the measurement apparatus. In this case, the measurement value, such as the two-dimensional distribution of the optical normal direction, can be calculated by similar processing to the first exemplary embodiment with use of the pixel numbers (Xp, Yp) in the image input to the projector 2101 as the pixel numbers (Xd, Yd) in the illumination apparatus 11 according to the first exemplary embodiment. In other words, the present exemplary embodiment can be realized by replacing Xd and Yd with Xp and Yp, respectively, in the description of the first exemplary embodiment.

As described above, the measurement system 100 according to the fifth exemplary embodiment uses the projector 2101 and screen 2102, which can be easily enlarged, instead of the display. By this configuration, the measurement system can expand the range where the measurement system can measure the optical normal direction of the measurement object 15 by measuring it once, thereby acquiring the normal direction distribution in a further wider angular range.

In the above-described exemplary embodiments, the measurement system has been described as being configured to derive the reflection characteristic of the measurement object 15. A measurement system according to a sixth exemplary embodiment will be described as a measurement system 100 equipped with an evaluation function of comparing a result of measuring a reference sample and a result of measuring an evaluation sample and determining whether a difference therebetween falls within a predetermined range. The sixth exemplary embodiment is similar to the first exemplary embodiment in terms of each configuration thereof but is different from the measurement system according to the first exemplary embodiment in terms of a processing procedure and a functional configuration thereof.

Figure 19:
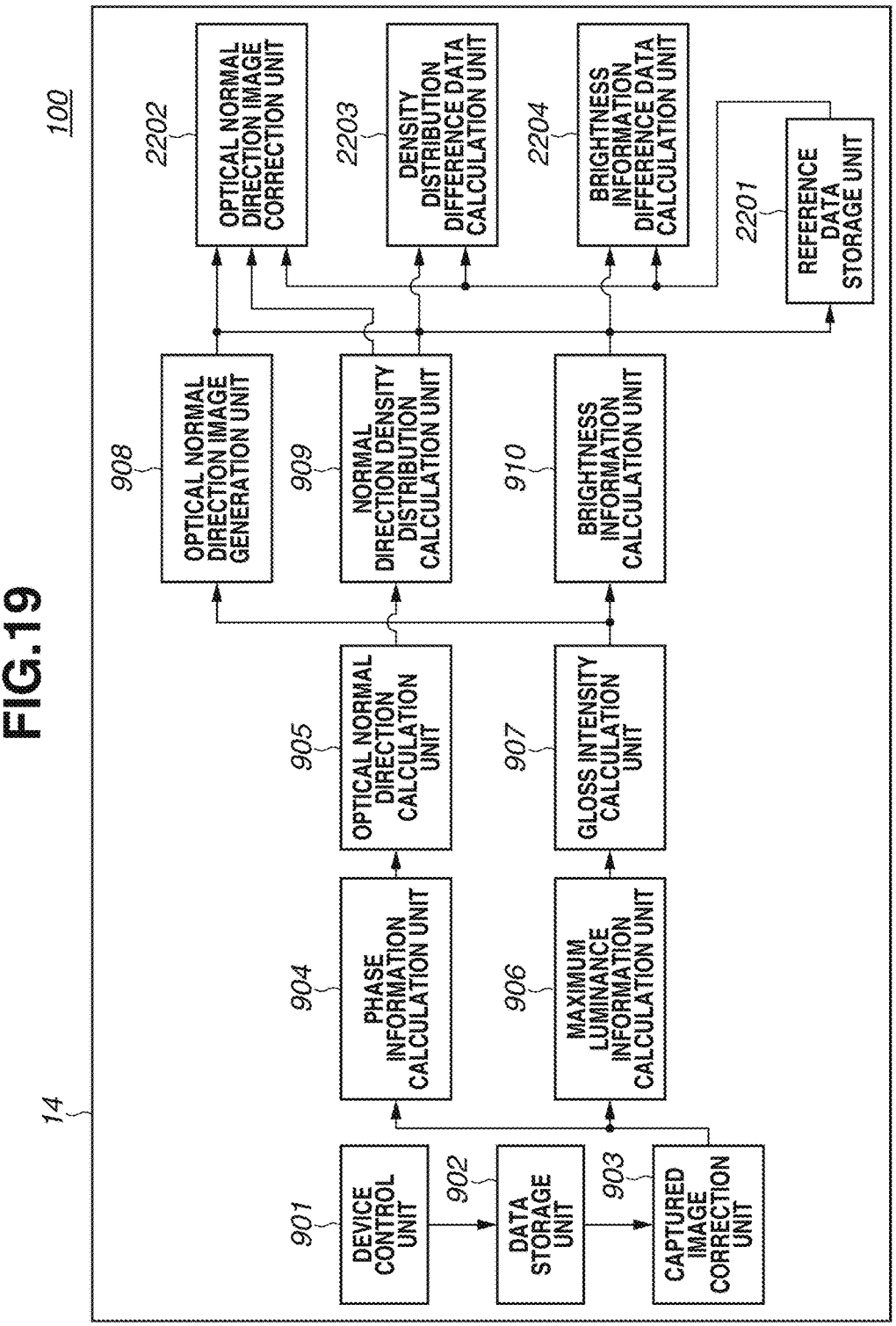
FIG. 19 is a block diagram illustrating a functional configuration of a measurement apparatus according to a sixth exemplary embodiment.

FIG. 19 is a block diagram illustrating a functional configuration of the information processing apparatus 14 according to the sixth exemplary embodiment. The information processing apparatus 14 according to the sixth exemplary embodiment includes a reference data storage unit 2201, an optical normal direction image correction unit 2202, a density distribution difference data calculation unit 2203, and a brightness information difference data calculation unit 2204 in addition to the configuration according to the first exemplary embodiment. The optical normal direction image generation unit 908, the normal direction density distribution calculation unit 909, and the brightness information calculation unit 910 according to the sixth exemplary embodiment generate and calculate an optical normal direction image, a normal direction density distribution, and brightness information of the reference sample, respectively, and store them into the reference data storage unit 2201. The optical normal direction image generation unit 908 according to the sixth exemplary embodiment generates an optical normal direction image of the evaluation sample, and outputs the generated image to the optical normal direction image correction unit 2202.

The normal direction density distribution calculation unit 909 according to the sixth exemplary embodiment calculates a normal direction density distribution for the evaluation sample. The normal direction density distribution calculation unit 909 outputs the calculated distribution to the density distribution difference data calculation unit 2203 and the optical normal direction image correction unit 2202. The brightness information calculation unit 910 according to the sixth exemplary embodiment calculates brightness information of the evaluation sample. The brightness information calculation unit 910 outputs the calculated information to the brightness information difference data calculation unit 2204. The optical normal direction image correction unit 2202 corrects the optical normal direction image based on the normal direction density distribution for the reference sample that is stored in the reference data storage unit 2201 and the normal direction density distribution for the evaluation sample that is calculated by the normal direction density distribution calculation unit 909. The optical normal direction image correction unit 2202 outputs the optical normal direction image after the correction.

Figure 20:
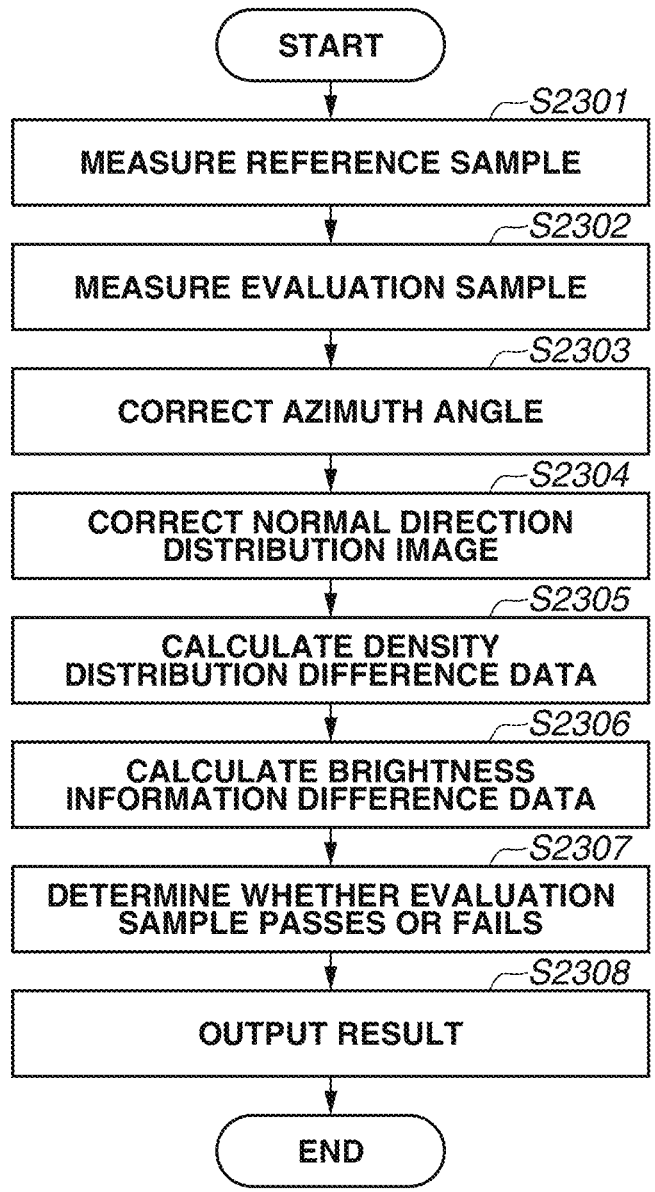
FIG. 20 is a flowchart illustrating processing according to the sixth exemplary embodiment.

FIG. 20 is a flowchart illustrating processing performed by the information processing apparatus 14 according to the sixth exemplary embodiment. First, in step S2301, the information processing apparatus 14 measures a reflection characteristic of the reference sample. A measurement procedure therefor is similar to the measurement procedure according to the first exemplary embodiment that has been described with reference to FIG. 3A. In other words, in this step, the information processing apparatus 14 calculates the optical normal direction distribution image, the normal direction density distribution, and the brightness information of the reference sample.

In step S2302, the information processing apparatus 14 measures a reflection characteristic of the evaluation sample. A measurement procedure in step S2302 is also similar to the first exemplary embodiment, similarly to step S2301. Therefore, in this step, the information processing apparatus 14 calculates the optical normal direction distribution image, the normal direction density distribution, and the brightness information of the evaluation sample.

In step S2303, the information processing apparatus 14 corrects an azimuth angle of the evaluation sample. An orientation of a sample relative to the measurement system 100 may be unintentionally changed every time the sample is measured. The X-axis direction and/or the Y-axis direction may shift between the reference sample and the evaluation sample. This shift does not raise a problem with an isotropic sample, the reflection characteristic of which is independent of the orientation of the sample. However, this shift affects the evaluation accuracy when it comes to an anisotropic sample. The azimuth angle is corrected based on the data of the normal direction density distribution calculated in step S307. In the present exemplary embodiment, the normal direction density distribution data is acquired while the azimuth angle of the evaluation sample is rotated degree by degree, and a difference from the normal direction density distribution data of the reference sample is calculated. An angle at which the difference is minimized is calculated as a correction angle, and the azimuth angle of the evaluation sample is corrected according to the correction angle. The correction of the azimuth angle is expected to bring about a similar effect to rotating the evaluation sample in the XY directions and measuring the evaluation sample when the evaluation sample is located in a direction where the evaluation sample attains a reflection characteristic closest to the reference sample. The measurement system 100 according to the present exemplary embodiment compares the reflection characteristic of the reference sample and the reflection characteristic of the evaluation sample based on the measured value in which the azimuth angle is corrected in this manner.

In step S2304, the information processing apparatus 14 corrects the normal direction distribution image of the evaluation sample based on the correction angle calculated in step S2303. When a result is output in step S2308, which will be described below, the normal direction image of the reference sample and the normal direction image of the evaluation sample after the correction are displayed next to each other. This display allows the user to visually recognize a tendency of the difference between the reference sample and the evaluation sample.

In step S2305, the information processing apparatus 14 calculates difference data between the normal direction density distribution for the reference sample and the normal direction density distribution for the evaluation sample. The difference data may be a difference for each of the sections of the azimuth angle and the zenith angle, or may be data acquired by calculating a square root of a sum of squares of differences in all of the sections. In step S2306, the information processing apparatus 14 calculates difference data between the brightness information of the reference sample and the brightness information of the evaluation sample. The difference data is, for example, a difference in the average value and/or a difference in the standard deviation of cluster sizes indicated by the brightness information, and/or a difference in the number of clusters larger in size than the predetermined size. In step S2307, the information processing apparatus 14 compares each of the pieces of difference data calculated in steps S2305 and S2306 with passing/failing determination reference data, and determines whether the evaluation sample passes or fails. The passing/failing determination reference data is set in advance by, for example, being input from outside via the general-purpose I/F 206. When determining whether the evaluation sample passes or fails, for example, the information processing apparatus 14 determines that the evaluation sample passes if the difference data is smaller than the passing/failing determination reference data, and otherwise determines that the evaluation sample fails. Lastly, in step S2308, the information processing apparatus 14 outputs a result of the determination. The information processing apparatus 14 outputs the various kinds of difference data in addition to the result of the determination.

As described above, the measurement system according to the sixth exemplary embodiment is equipped with the function of evaluating the reflection characteristic. By this capability, the difference from the reference sample can be easily evaluated with respect to the reflection characteristic due to the difference(s) in the two-dimensional distribution of the optical normal direction and/or the gloss intensity distribution.

In a seventh exemplary embodiment, a measurement system will be described as being configured to measure parameters in a reflection model related to the spatially varying bidirectional reflectance distribution function (SVBRDF), which is a two-dimensional distribution of the bidirectional reflectance distribution function (BRDF). Similar configurations to the above-described exemplary embodiments will not be described in detail below. The BRDF is a four-dimensional function of an illumination direction ωi (θi, φi) and an observation direction ωo (θo, φo), and indicates how much light is reflected in each direction when the light is incident on a surface of an object from an arbitrary direction. The SVBRDF is a six-dimensional function including positional variables Pxy (X, Y) in addition to the above-described four variables in the BRDF. The number of dimensions is large, whereby measuring each of the variables in detail results in an enormous data amount and also requires a long time for the measurement. Further, the SVBRDF requires detection of even an extremely small light amount susceptive to an influence of noise, which makes accurate measurement difficult. On the other hand, there are proposed a large number of reflection models that express the BRDF with use of fewer parameters. The SVBRDF more closely approximated to the reflection model can be acquired by measuring two-dimensional distributions of these parameters. The measurement system 100 according to the seventh exemplary embodiment derives the SVBRDF by measuring the parameters in the reflection model expressing the BRDF of the measurement object 15. When the SVBRDF can be acquired, it is possible to predict how the measurement object 15 would appear when being illuminated under an arbitrary condition and observed from an arbitrary direction.

The reflection model of the BRDF calculated by the measurement system according to the present exemplary embodiment will be described. In the reflection model, reflected light I is expressed by a sum of a diffuse reflection component Id and a specular reflection component Is, as indicated by the following equation (44).

$$I = Id + Is \quad (44)$$

In a reflection model using the Lambert's model, the diffuse reflection component Id of the reflected light is provided as indicated by the following equation (45).

$$Id(X,Y,\theta i,\varphi i) = Rd(X,Y) \times Ein(\theta i,\varphi i) \times \cos(\theta i) \quad (45)$$

In this equation (45), Ein represents an intensity of illumination light. Rd represents a reflectance of the diffuse reflection component (hereinafter referred to as a diffuse reflectance). Rd is a ratio between a luminance level $Id_{smp}$ of when, for example, the light is emitted from 0 degrees and received at 45 degrees with respect to the measurement surface, and a luminance level $Id_{std}$ from a reference diffuse reflection surface acquired under the same conditions. Rd includes a correction of a black level with use of a luminance level $Id_{bk}$ of when the imaging is carried out with the illumination turned off or the light therefrom blocked. Rd includes scaling with use of a value $Cal_{Rd045}$ of the diffuse reflectance of when the light is emitted from 0 degrees and received at 45 degrees with respect to the reference diffuse reflection surface. In this case, the diffuse reflectance Rd is provided as indicated by the following equation (46).

$$Rd(X,Y) = \frac{Id_{smp}(X,Y) - Id_{bk}(X,Y)}{Id_{std}(X,Y) \times Cal_{Rd045}} \quad (46)$$

A pressed surface of barium sulfate powder or polytetrafluoroethylene (PTFE) powder can be used as the reference diffuse reflection surface. A value determined by an official measuring institution can be used as the value of $Cal_{Rd045}$. The specular reflection component is the component generated due to the reflection of the incident light on the top of the measurement surface. The specular reflection component is observed with a high intensity in a specific reflection direction (the above-described maximum reflection direction) and a direction around that. In a reflection model modified from the Torrance-Sparrow model, the specular reflection component of the reflected light is expressed by the following equation (47).

$$Is(X,Y,\theta i,\varphi i,\theta o,\varphi o) = F(X,Y,\theta i) \times D(X,Y,\theta i,\varphi i,\theta o,\varphi o) \times Ein/\cos(\theta o) \quad (47)$$

In this equation (47), Ein represents the intensity of the illumination light, F represents a function indicating a Fresnel reflection, and D represents a function indicating gloss image clarity. Details of the gloss image clarity will be described below. The Fresnel reflection refers to such a phenomenon that the reflectance changes depending on the direction of the incident light or the reflected light, and the reflectance increases as the zenith angle approaches 90 degrees. The function F is expressed by the following equation (48).

$$F(X,Y,\theta i,\varphi i) = 1 - (1 - Rs(X,Y)) \times W(\theta i,\varphi i) \quad (48)$$

Rs represents a specular reflectance measured by the measurement system according to the present exemplary embodiment. The specular reflectance is a reflectance at a zenith angle θm expressed by the following equation (49).

$$\theta m = \arccos(V \cdot Nv) \quad (49)$$

In this equation (49), V represents a vector indicating the light reception direction. V is the zenith angle of 45 degrees and the azimuth angle of 0 degrees in the measurement system. Nv represents the vector indicating the optical normal direction measured by the measurement system. A symbol "·" represents an inner product of the vectors, and θm represents an angle formed between V and Nv.

W in the equation (48) is a ratio between the reflectance of the Fresnel reflection at the measured zenith angle θm, and the reflectance of the Fresnel reflection at an angle θv formed between the illumination direction ωi (θi, φi) and the optical normal direction Nv. W is calculated with use of an equation (50).

$$W = \frac{(1 - \cos(\theta v))^5}{(1 - \cos(\theta m))^5} \quad (50)$$

In this equation (50), θv is acquired according to the following equation (51).

$$\theta v = \arccos(\omega i \cdot Nv) \quad (51)$$

In the equation (51), ωi represents the vector indicating the illumination direction.

D in the above-described equation (47) represents a distribution of a line normal to an extremely small surface. D is related to the gloss image clarity. In the Torrance-Sparrow reflection model, a surface of an object is assumed to be formed from a group of extremely small surfaces that cause specular reflections, and diffusion in each direction is expressed based on a distribution of a direction normal to this extremely small surface. This reflection model uses the distribution model proposed by Trowbridge-Reitz, which is expressed by the following equation (52), as a function indicating this distribution of the normal direction.

$$D = \left(\frac{\alpha^2}{\cos(\theta g)^2 \times (\alpha^2 - 1) + 1}\right)^2 \quad (52)$$

In this equation (52), α is a parameter related to a shape of the distribution, and indicates a value of the measured gloss image clarity. As described above, the gloss image clarity is a feature quantity related to the change in the intensity of the reflected light in the specular reflection direction and a direction around that.

Figure 11:
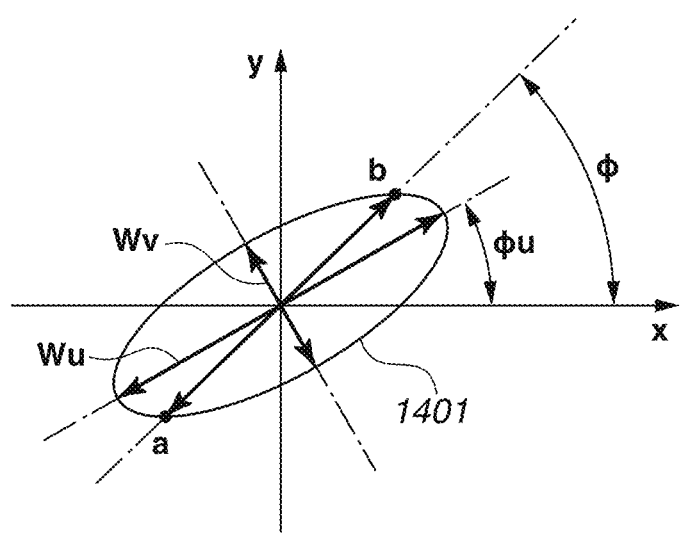
FIG. 11 is a schematic view illustrating an expression of gloss anisotropy with use of an ellipse.

A characteristic that the gloss image clarity changes depending on the azimuth angle is called gloss anisotropy. On a surface exhibiting the gloss anisotropy, an observed light amount changes even with the illumination direction and the light reception direction fixed when this surface is rotated around a line normal to the surface. For example, a metal processed by a hairline finish, and a satin embroidery having a regularly folded rough-surfaced structure exhibit the gloss anisotropy. Typically, an azimuth angle at which the gloss image clarity is maximized and an azimuth angle at which the gloss image clarity is minimized are orthogonal to each other, and the gloss image clarity smoothly changes across azimuth angles therebetween. Such a characteristic of the gloss anisotropy is approximately expressed by a model using an ellipse. According to this ellipse model, the gloss anisotropy is modeled by setting the azimuth angle at which the gloss image clarity is maximized as a long-axis direction of the ellipse, and associating a value of the gloss image clarity at this azimuth angle with a length of the long axis of the ellipse and a value of the gloss image clarity in a direction orthogonal to this azimuth angle with a length of a short axis of the ellipse. A value of the gloss image clarity in a direction at an arbitrary azimuth angle φ is calculated from a length of a line segment connecting two intersection points between the above-described ellipse and a straight line of the azimuth angle φ that passes through a center of this ellipse. FIG. 11 is a schematic view illustrating the above-described ellipse model. An ellipse 1401 expresses gloss anisotropy in which φu is the azimuth angle at which the gloss image clarity is maximized, αu is a value of the gloss image clarity in a direction at φu, and αv is a value of the gloss image clarity in a direction orthogonal to φu. The gloss image clarity at the arbitrary azimuth angle φ is provided in the form of a value corresponding to a length of a line segment ab illustrated in FIG. 11.

A value of the parameter α in the equation (52) is 1 or a smaller value, and is negatively correlated with the gloss image clarity. Therefore, as the parameter α reduces, this indicates higher gloss image clarity. The measurement system according to the seventh exemplary embodiment measures the azimuth angle φu at which the parameter α in the equation (52) is minimized, the value αu of the parameter α for the direction at φu, and the value αv of the parameter α for the direction perpendicular to φu. The parameter α representing the gloss image clarity under the illumination direction ωi and the observation direction ωo can be calculated with use of the above-described parameters φu, αu, and αv.

(Configuration of Measurement Apparatus)

Figure 22:
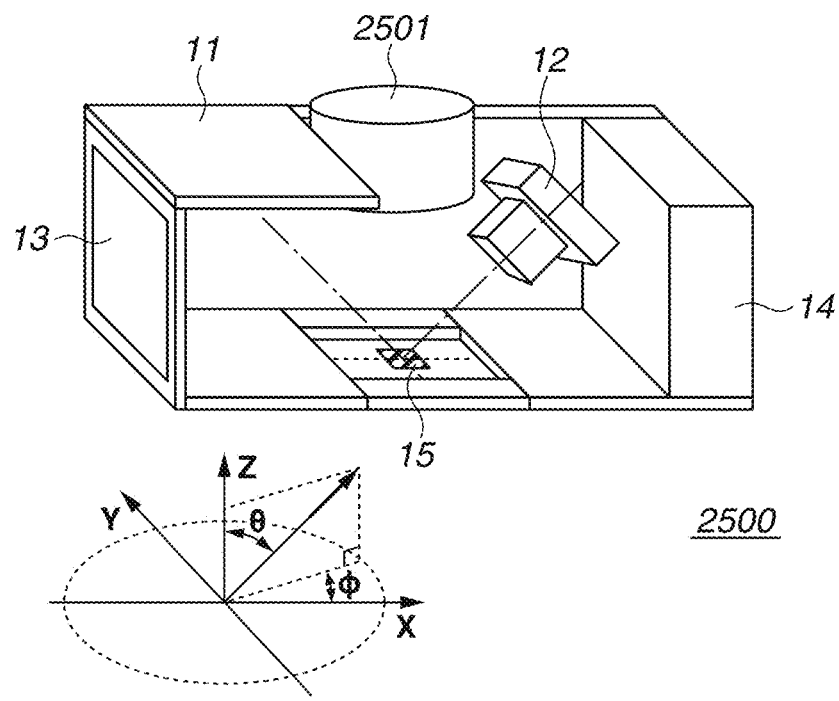
FIG. 22 is a schematic view illustrating an external appearance of a measurement apparatus according to a seventh exemplary embodiment.

FIG. 22 is a diagram illustrating an external appearance of the measurement system according to the seventh exemplary embodiment. A measurement system 2500 includes an illumination apparatus 2501 for measuring the diffuse reflectance in addition to the configuration according to the first exemplary embodiment. The illumination apparatus 2501 illuminates the surface of the measurement object 15 with parallel light from a direction at a zenith angle of 0 degrees. A light source for the illumination can be embodied with use of a light-emitting diode (LED), halogen, xenon, or the like. The light source may have a high color rendering property, may be bright, may keep the luminance changeability low over time, and may achieve a low unevenness in a plane.

The imaging apparatus 12 is configured similarly to the first exemplary embodiment. The imaging apparatus 12 images the measurement object 15 illuminated by the illumination apparatus 2501 in addition to the measurement object 15 illuminated by the illumination apparatus 11. When the measurement object 15 is imaged while being illuminated by the illumination apparatus 11, the illumination apparatus 2501 is turned off or the light therefrom is blocked. On the other hand, when the measurement object 15 is imaged while being illuminated by the illumination apparatus 2501, the illumination apparatus 11 is turned off or the light therefrom is blocked. The imaging is also carried out even in such a state that both the illumination apparatus 11 and the illumination apparatus 2501 are turned off or the light beams from both of them are blocked. Hereinafter, the captured image acquired by imaging the measurement object 15 illuminated by the illumination apparatus 11 will be referred to as a diffuse reflection captured image, and the captured image acquired by imaging the measurement object 15 illuminated by the illumination apparatus 2501 will be referred to as a specular reflection captured image. The captured image acquired by carrying out the imaging with both the illumination apparatuses 11 and 2501 turned off or the light beams from both of them blocked will be referred to as a black level captured image. The information processing apparatus 14 according to the present exemplary embodiment controls the illumination apparatus 2501 described above in addition to the illumination apparatus 11 and the imaging apparatus 12 to acquire the captured images of the measurement object 15. The information processing apparatus 14 performs calculation processing that will be described below on the captured images, and calculates the parameters in the above-described reflection model. The information processing apparatus 14 outputs a processing progress and a processing result of the calculation processing to the operation panel 13 and/or a not-illustrated external apparatus.

(Overview of Measurement Method)

The diffuse reflectance Rd is calculated with use of the above-described equation (46) based on the captured image of the measurement object 15 illuminated by the illumination apparatus 2501. The optical normal direction Nv is calculated in a similar manner to the first exemplary embodiment.

Figure 29:
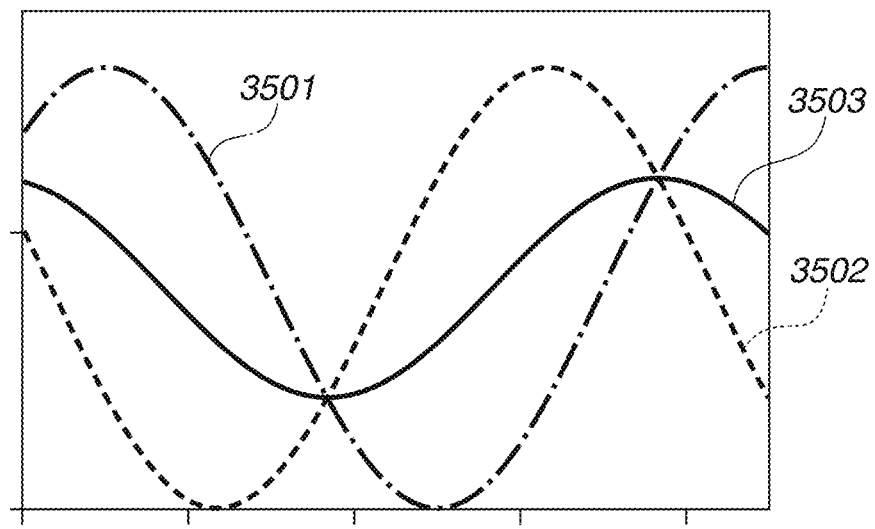
FIG. 29 is a schematic view illustrating a combination of modulated signals out of phase with each other.
Figure 31A:
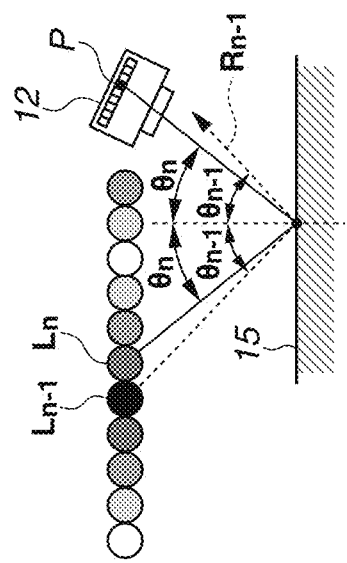
FIGS. 31A and 31B are schematic views each illustrating a relationship between illumination light and reflected light received by the imaging apparatus.
Figure 31B:
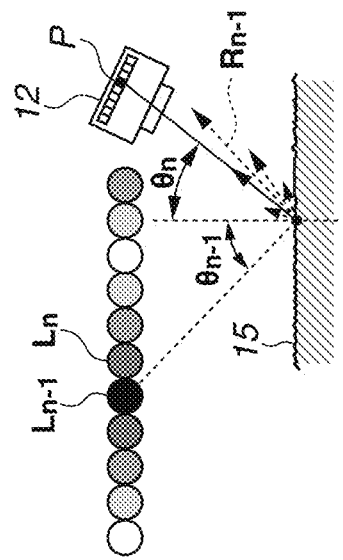

A method for measuring the gloss image clarity will be described. The gloss image clarity is an index related to how much, in a glossy object, an image appearing therein is clear. If the value of the gloss image clarity of the object is high, the image of the illumination appearing in the object is clearly observed. On the contrary, if the value of the gloss image clarity of the object is low, the image of the illumination appearing in the object is observed in a blurred state. FIGS. 31A and 31B are schematic views illustrating a relationship between the illumination light and the reflected light received by the imaging apparatus 12. FIG. 31A illustrates a relationship between the illumination light and the received reflected light when the measurement surface is smooth and the gloss image clarity is high. If the image clarity of the measurement surface is high, the illumination direction of the illumination light leading to the reflected light reflected in the light reception direction is dominated by a specific direction leading to the specular reflection with respect to the light reception direction. The sensor pixel P of the imaging apparatus 12 in FIG. 31A receives only the reflected light of the illumination light from the light source Ln, which is in the specular reflection relationship with the light reception direction. The illumination light from a light source Ln-1 is reflected in a direction Rn-1, and is not received by the imaging apparatus 12. On the other hand, if the measurement surface is rough and the image clarity is low, the reflected light is scattered. Therefore, the illumination direction of the illumination light leading to the reflected light reflected in the light reception direction ranges over a width around the direction leading to the specular reflection with respect to the light reception direction. As the image clarity reduces, this width increases. FIG. 31B illustrates a relationship between the illumination light and the received reflected light when the gloss image clarity of the surface of the measurement object 15 is low. In FIG. 31B, the illumination light from the light source Ln-1 is reflected not only in the direction Rn-1 but also in a direction around that. The sensor pixel P of the imaging apparatus 12 also receives the reflected light of the illumination light from the light source Ln-1 in addition to the reflected light of the illumination light from the light source Ln. As a result, the received reflected light is constituted by a combination of reflected light beams from illumination light beams from directions out of phase with each other. FIG. 29 is a schematic view illustrating a combination of modulated signals out of phase with each other. A signal 3501 and a signal 3502 illustrated in FIG. 29 are sinusoidal modulated signals out of phase with each other, and a signal 3503 is a modulated signal generated by combining the signal 3501 and the signal 3502. As understood from FIG. 29, combining the modulated signals out of phase with each other results in a reduction in an amplitude. In other words, as the gloss image clarity of the measurement object 15 reduces, the amplitude of the change in the luminance at the pixel in the captured images reduces. The amplitude information is converted into the gloss image clarity by referring to a gloss image clarity conversion table, in which a correspondence relationship therebetween is described, and using a known interpolation method. FIG. 28B is a diagram illustrating an example of the gloss image clarity conversion table. The gloss image clarity conversion table is created in advance based on a sample having known gloss image clarity. The measurement system 2500 according to the present exemplary embodiment carries out the imaging while modulating the luminances of the plurality of point light sources, and calculates the amplitude information that is an amplitude component of the change in the luminance at the image pixel in the captured images, thereby calculating the gloss image clarity of the measurement object 15.

A method for measuring the specular reflectance Rs will be described. The above-described bias information C indicates an average value of intensities of reflected light beams around the specular reflection direction. The reflected light beams corresponding to the bias information C also include the diffuse reflection component. Bias information Cs with the diffuse reflection component subtracted therefrom is calculated with use of the following equation (53), assuming that Csmp represents the bias information C of the measurement surface, Cstd represents the bias information C of the reference diffuse reflection surface, and $Rd_{smp}$ represents the diffuse reflectance Rd of the measurement surface.

$$Cs = Csmp - Cstd \times \frac{Rd_{smp}}{Cal_{R045}} \qquad (53)$$

In the equation (53), $Cal_{R045}$ is the reflectance when the light is emitted from 0 degrees and is received at 45 degrees with respect to the reference diffuse reflection surface. The specular reflection components are distributed around the specular reflection direction based on the distribution of the line normal to the extremely small surface. The calculated specular reflectance Rs relates to the reflected light in the specular reflection direction, which is a center of the distribution of the line normal to the extremely small surface. A shape of the distribution of the specular reflection component is provided as indicated by the above-described function D. Therefore, the function D is integrated with respect to all of the reflection directions, and an average value Dave is calculated. Bias information Csd corresponding to the reflected light in the specular reflection direction can be calculated with use of the following equation (54) from a ratio between the average value Dave and a value Ds of the function D for the specular reflection direction.

$$Csd = Cs \times \frac{Ds}{Dave} \qquad (54)$$

When the function D is provided as indicated by the above-described equation (52), the value of Ds is 1. On the other hand, the average value Dave, which is dependent on the parameters αu and αv, is calculated by preparing in advance a specular reflection conversion table, in which a value of the average value Dave corresponding to the discretely presented parameters αu and αv is described, referring to this conversion table, and using a known interpolation method. FIG. 28A illustrates an example of the specular reflection conversion table. The specular reflection conversion table is created in advance based on the above-described equation (52). The value of the specular reflectance Rs is calculated with use of the following equation (55) from the value of Csd of the measurement surface, a value $Cstd_s$ of the bias information C of the reference specular reflection surface, and the value $Cal_{Rs45}$ of the Fresnel reflectance in the direction at 45 degrees with respect to the reference specular reflection surface.

$$Rs = \frac{Csd}{Cstd_s} \times Cal_{Rs45} \qquad (55)$$

A black polished glass made of an optical glass BK7 can be used as the reference specular reflection surface. A value determined by an official measuring institution can be used as the value of $Cal_{Rs45}$.

(Control of Illumination Apparatus 2501)

The illumination apparatus 2501 for measuring the diffuse reflectance illuminates the measurement object 15 with the illumination light kept even over the entire surface. Similarly to the above-described exemplary embodiments, the illumination images displayed by the illumination apparatus 11 are the images holding the luminance information modulated across multiple tones according to the periodic functions for each of the source pixels. The luminance L at each of the source pixels in the illumination images displayed by the illumination apparatus 11 is provided as indicated by the above-described equation (2). However, in the seventh exemplary embodiment, patterns of three groups are used for the direction in which the phase is changed. More specifically, the illumination images used in the seventh exemplary embodiment are the illumination images in the first group in which the phase is changed in the X direction, the illumination images in the second group in which the phase is changed in the Y direction, and illumination images in a third group in which the phase is changed in a direction forming −45 degrees together with the X axis. By using them, the measurement system 2500 derives three kinds of gloss image clarity at different azimuth angles. The measurement object 15 is illuminated with use of the illumination images in the first to third groups for acquiring the above-described azimuth angle φu and the values of gloss image clarity corresponding to the lengths of the long axis and the short axis of the above-described ellipse from the three kinds of gloss image clarity. The measurement system 2500 acquires the gloss image clarity at each of the azimuth angle of 0 degrees, the azimuth angle of 90 degrees, and the azimuth angle of 45 degrees. The phase distribution functions δ of the illumination patterns of the first and second groups are provided as indicated by the above-described equations (3) and (4). A phase distribution function δ of the illumination pattern of the third group is provided as indicated by the following equation (56).

$$\delta(Xd,Yd)=K5\times(Xd/\sqrt{2}-Yd/\sqrt{2}) \quad (56)$$

In this equation (56), K5 is a constant, and may have, for example, a value of 1. The number of illumination images for the luminance modulation is 3 for any of the groups, and the gloss anisotropy is calculated by carrying out the measurement at least nine times in total for the three groups. FIGS. 30A to 30M are schematic views illustrating an example of the illumination images when the number of illumination images is n=4. FIG. 30A illustrates a positional relationship between the illumination apparatus 11 and the illumination pattern. FIGS. 30B to 30E illustrate the illumination pattern of the first group, FIGS. 30F to 30I illustrate the illumination pattern of the second group, and FIGS. 30J to 30M illustrate the illumination pattern of the third group.

(Functional Configuration of Information Processing Apparatus 14)

Figure 32:
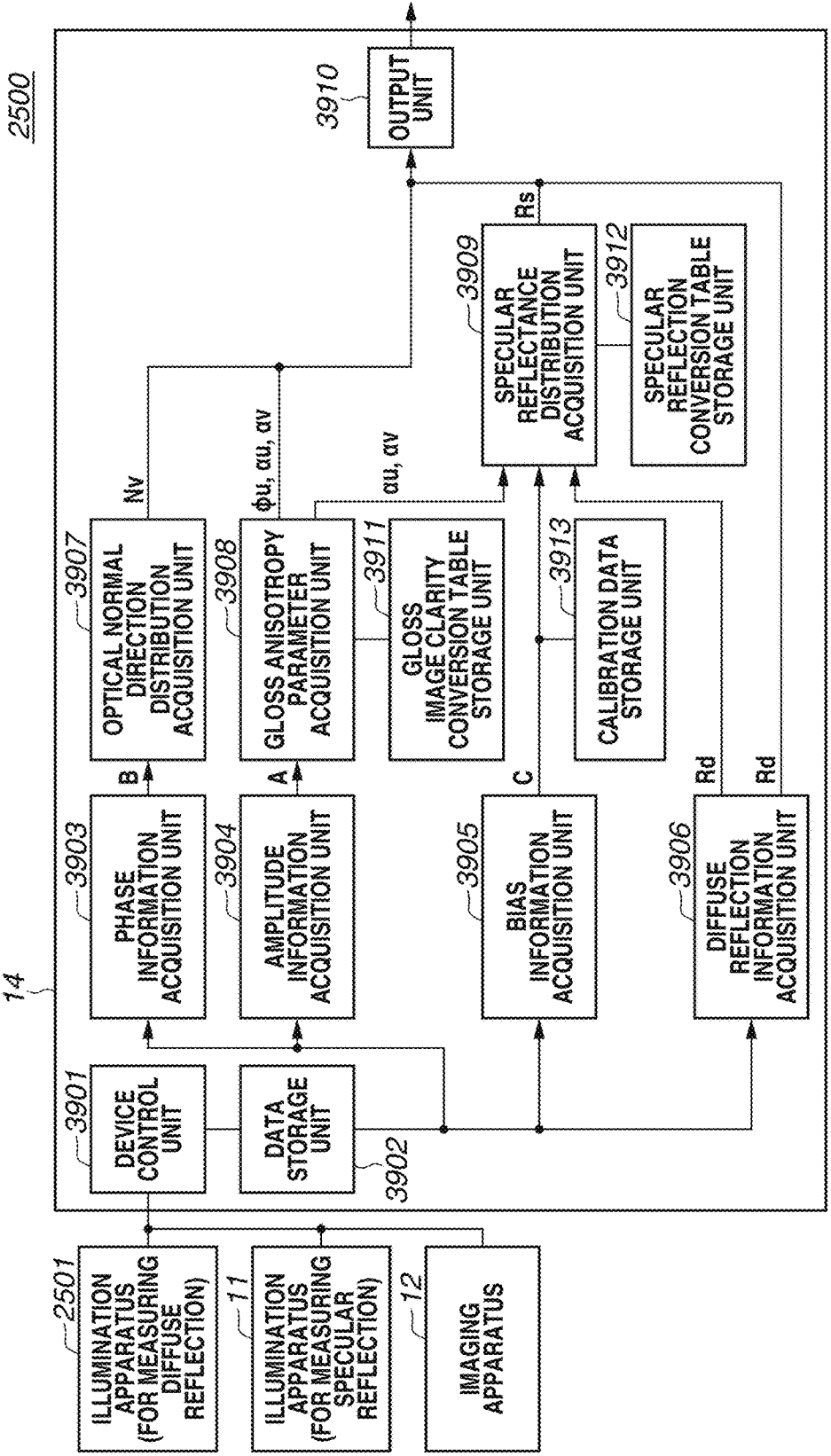
FIG. 32 is a block diagram illustrating a functional configuration according to the seventh exemplary embodiment.

A detailed configuration of the information processing apparatus 14 will be described. FIG. 32 is a block diagram illustrating a functional configuration of the information processing apparatus 14 according to the present exemplary embodiment. A device control unit 3901 controls the illumination apparatus 11 and the imaging apparatus 12, similarly to the device control unit 901 according to the first exemplary embodiment. The device control unit 3901 controls the illumination apparatus 2501 for measuring the diffuse reflection. A data storage unit 3902 stores the acquired captured images, similarly to the data storage unit 902.

A phase information acquisition unit 3903 calculates the phase information at each of the sensor pixels based on the nine captured images acquired by imaging the measurement object 15 illuminated with use of the illumination images in the first to third groups that are stored in the data storage unit 3902, and acquires the phase distribution for each of the groups. An amplitude information acquisition unit 3904 calculates the amplitude of the change in the luminance at each of the sensor pixels based on the captured images of the measurement object 15 illuminated with use of the illumination images in the first to third groups that are stored in the data storage unit 3902, and derives the amplitude distribution for each of the groups.

A bias information acquisition unit 3905 calculates the bias information at each of the sensor pixels based on the captured images of the reference diffuse reflection surface illuminated with use of the illumination images in the first group that are stored in the data storage unit 3902, and acquires the bias distribution. The bias distribution for the reference diffuse reflection surface is stored in a calibration data storage unit 3913. The bias information acquisition unit 3905 calculates the bias information for each of the sensor pixels based on the captured images of the reference specular reflection surface illuminated with use of the illumination images in the first group that are stored in the data storage unit 3902, and acquires the bias distribution. The bias distribution for the reference specular reflection surface is stored in the calibration data storage unit 3913. The bias information acquisition unit 3905 calculates the bias information for each of the sensor pixels based on the captured images of the measurement object 15 illuminated with use of the illumination images in the first group, and acquires the bias distribution for the measurement object 15. A diffuse reflection information acquisition unit 3906 acquires a two-dimensional distribution of the diffuse reflectance Rd based on the captured image of the measurement object 15 illuminated by the illumination apparatus 2501.

The information processing apparatus 14 includes an optical normal direction distribution acquisition unit 3907, a gloss anisotropy parameter acquisition unit 3908, and a gloss image clarity conversion table storage unit 3911. The optical normal direction distribution acquisition unit 3907 acquires the two-dimensional distribution of the optical normal direction Nv based on the phase distribution acquired by the phase information acquisition unit 3903. The gloss anisotropy parameter acquisition unit 3908 acquires two-dimensional distributions of the parameters φu, αu, and αv representing the gloss anisotropy based on the amplitude distribution acquired by the amplitude information acquisition unit 3904. In this processing, the gloss anisotropy parameter acquisition unit 3908 refers to the gloss image clarity conversion table stored in the gloss image clarity conversion table storage unit 3911. A specular reflectance distribution acquisition unit 3909 acquires a two-dimensional distribution of the specular reflectance Rs based on the bias distribution for the reference diffuse reflection surface, the bias distribution for the reference specular reflection surface, the two-dimensional distribution of the diffuse reflectance Rd, the two-dimensional distributions of the gloss anisotropy parameters φu, αu, and αv, and the bias distribution for the measurement object 15. The specular reflectance distribution acquisition unit 3909 refers to the specular reflection conversion table stored in a specular reflection conversion table storage unit 3912 in processing for acquiring the two-dimensional distribution of the specular reflectance Rs.

An output unit 3910 outputs the two-dimensional distributions of the parameters Rd, Rs, Nv, φu, αu, and αv in the reflection model, which are measurement results, and other intermediate data based on a user's instruction. In the above description, each of the units has been described as being configured to proceed to the next processing after completing the processing on all of the image pixels and acquiring the distribution image. However, each of the units may be configured to perform the entire processing pixel by pixel, or may be configured to complete the entire processing for a plurality of pixels at a time.

FIGS. 26A to 26D are flowcharts illustrating processing performed by the information processing apparatus 14 according to the present exemplary embodiment. The CPU 201 included in the information processing apparatus 14 reads out and executes a program for performing flowcharts that will be described below, by which each of the units illustrated in FIG. 32 is realized. In step S2901, the information processing apparatus 14 calibrates the measurement system 2500. The term calibration refers to the processes for acquiring the data of the reference surface and the black level that have been described above. In this step, the information processing apparatus 14 acquires the black level captured image, the diffuse reflection captured image of the reference diffuse reflection surface, and the bias distributions of the reference diffuse reflection surface and the reference specular reflection surface that have been described above. Details thereof will be described below.

In step S2902, the device control unit 3901 images and measures the measurement object 15. As described above, in the measurement system 2500 according to the present exemplary embodiment, the device control unit 3901 images the measurement object 15 that the illumination apparatus 2501 illuminates, and images the measurement object 15 that the illumination apparatus 11 illuminates while displaying the respective illumination images in the first group, the second group, and the third group.

In step S2903, the amplitude information acquisition unit 3904 acquires the amplitude distribution for the measurement object 15. The amplitude distribution is the image storing therein the value of the amplitude information A corresponding to each of the image pixels in the captured images. The amplitude of the change in the luminance at each of the sensor pixels is calculated for each of the groups with respect to the captured images captured while the illumination apparatus 11 displays the illumination images in the first to third groups on the display. As a result, three amplitude distributions are derived. The amplitude distributions calculated from the captured images based on the illumination images in the first to third groups are the amplitude distributions at the azimuth angle of 0 degrees, the azimuth angle of 90 degrees, and the azimuth angle of 45 degrees, respectively. The amplitude information A at each of the sensor pixels is calculated with use of the above-described equations (9), (10), and (11) from the luminance level Ii at each of the image pixels in the captured images and the modulation information Δi.

In step S2904, the phase information acquisition unit 3903 acquires the phase distribution for the measurement object 15. The phase distribution is the image storing therein the value of the phase information B corresponding to each of the image pixels in the captured images. The phase information acquisition unit 3903 performs similar processing to step S302 in the measurement procedure according to the first exemplary embodiment, and acquires the two phase distributions. In step S2905, the bias information acquisition unit 3905 acquires the bias distribution for the measurement object 15. The bias distribution is the image storing therein the value of the bias information C corresponding to each of the image pixels in the captured images. A bias distribution is calculated with use of the above-described equation (12) from the luminance level Ii at each of the sensor pixels, with use of the captured images captured while the illumination apparatus 11 displays the illumination images in the first group.

In step S2906, the diffuse reflection information acquisition unit 3906 calculates the two-dimensional distribution of the diffuse reflectance Rd. The diffuse reflectance Rd is calculated as indicated by the above-described equation (46). In the equation (46), $Id_{smp}$ is the luminance value in the diffuse reflection image acquired in step S2902. $Id_{bk}$ and $Id_{std}$ are the luminance value in the black level captured image, and the luminance value in the diffuse reflection captured image of the reference diffuse reflection surface acquired in step S2901, respectively.

In step S2907, the optical normal direction distribution acquisition unit 3907 derives the two-dimensional distribution of the optical normal direction Nv. The two-dimensional distribution of the optical normal direction Nv is acquired by performing similar processing to step S303 according to the first exemplary embodiment based on the two phase distributions acquired in step S2904. In step S2908, the gloss anisotropy parameter acquisition unit 3908 derives the two-dimensional distributions of the parameters expressing the gloss anisotropy. The two-dimensional distributions of the parameters expressing the gloss anisotropy are calculated based on the amplitude distribution acquired in step S2903. Details thereof will be described below. In step S2909, the specular reflectance distribution acquisition unit 3909 acquires the two-dimensional distribution of the specular reflectance Rs. The two-dimensional distribution of the specular reflectance Rs is calculated based on the bias distributions of the reference diffuse reflection surface and the reference specular reflection surface acquired in step S2901, the bias distribution acquired in step S2905, and the two-dimensional distribution of the diffuse reflectance Rd acquired in step S2906. Details thereof will be described below.

Lastly, in step S2910, the output unit 3910 outputs the various kinds of measurement results based on the user's instruction. Then, the processing is ended. The output items may include the intermediate data, such as the vector V indicating the light reception direction, the amplitude information distribution, the phase information distribution, the bias information distribution, and the captured images, besides the two-dimensional distributions of the parameters Rd, Rs, Nv, φu, αu, and αv in the reflection model.

The calibration processing procedure in step S2901 will be described in detail. FIG. 26B is a flowchart illustrating the calibration processing. In step S3001, the device control unit 3901 causes the illumination apparatus 2501 to illuminate the reference diffuse reflection surface and the imaging apparatus 12 to image the measurement object 15, thereby acquiring the diffuse reflection captured image. In step S3002, the device control unit 3901 transfers the illumination images in the first group to the illumination apparatus 11 to cause the illumination apparatus 11 to display them, and images the reference diffuse reflection surface. In step S3003, the device control unit 3901 transfers the illumination images in the first group to the illumination apparatus 11 to cause the illumination apparatus 11 to display them, and images the reference specular reflection surface.

In step S3004, the information processing apparatus 14 carries out the imaging with both the illumination apparatus 11 and the illumination apparatus 2501 turned off or the light beams from both of them blocked, thereby acquiring the black level captured image. In step S3005, the information processing apparatus 14 acquires the bias distribution for the reference diffuse reflection surface. The bias distribution is acquired by performing the processing in the above-described step, step S2905. In step S3006, the information processing apparatus 14 acquires the bias distribution for the reference specular reflection surface. The bias distribution is acquired by performing the processing in above-described step, step S2905. The minimum number of times of the imaging required for the calibration processing is eight in total, among which one is for the imaging of the diffuse reflection captured image of the reference diffuse reflection surface, three for the imaging with use of the illumination images in the first group for the reference diffuse reflection surface, three for the imaging with use of the illumination images in the first group for the reference specular reflection surface, and one for the imaging of the black level captured image. In other words, according to the measurement system 2500 according to the present exemplary embodiment, the SVBRDF can be acquired from the captured images acquired by carrying out the imaging seventeenth times at least, including the imaging of the measurement surface.

Details of the processing for calculating the two-dimensional distributions of the parameters expressing the gloss anisotropy in step S2908 will be described. FIG. 26D is a flowchart illustrating the processing for calculating the parameters expressing the gloss anisotropy. In step S3803, the information processing apparatus 14 acquires the two-dimensional distribution of the gloss image clarity. The gloss image clarity is calculated by referring to the above-described gloss image clarity conversion table based on the amplitude information A, which is the pixel value in the amplitude distribution acquired in step S2903, and using the known interpolation method. As the two-dimensional distribution of the gloss image clarity, the two-dimensional distributions of the gloss image clarity at the azimuth angle of 0 degrees, the azimuth angle of 90 degrees, and the azimuth angle of 45 degrees are acquired from the amplitude distributions at the azimuth angle of 0 degrees, the azimuth angle of 90 degrees, and the azimuth angle of 45 degrees, respectively.

In step S3804, the information processing apparatus 14 acquires the two-dimensional distributions of the parameters expressing the gloss anisotropy. In the present exemplary embodiment, the three parameters, the azimuth angle φu at which the parameter α in the equation (52) is minimized, the value αu of α for the direction at the azimuth angle φu, and the value αv of α for the direction orthogonal to φu are acquired as the parameters expressing the gloss anisotropy.

The respective values of the parameters φu, αu, and αv are provided as indicated by the following equations (57) to (59).

$$\phi u = \frac{\arctan\left(\frac{P3}{P1-P2}\right)}{2} \quad (57)$$

$$\alpha u = \frac{1}{\sqrt{\left(\frac{(P1+P2)-\sqrt{(P1-P2)^2+P3^2}}{2}\right)}} \quad (58)$$

$$\alpha v = \frac{1}{\sqrt{\left(\frac{(P1+P2)+\sqrt{(P1-P2)^2+P3^2}}{2}\right)}} \quad (59)$$

In the equations (57) to (59), values of P1, P2, and P3 are acquired according to the following equations (60) to (62).

$$P1 = -4 \times S90^2/P4 \quad (60)$$

$$P2 = -4 \times S0^2/P4 \quad (61)$$

$$P3 = -4 \times (S0^2 + S90^2 - 2 \times S45^2)/P4 \quad (62)$$

In the equations (60) to (62), a value of P4 is acquired according to the following equation (63).

$$P4 = (S0^2 + 2 \times S0 \times S90 + S90^2 - 2 \times S45^2) \times (S0^2 - 2 \times S0 \times S90 + S90^2 - 2 \times S45^2) \quad (63)$$

S0, S90, and S45 are the values of the gloss image clarity at the azimuth angle of 0 degrees, the azimuth angle of 90 degrees, and the azimuth angle of 45 degrees, respectively, and the values at the pixels in the two-dimensional distributions of the gloss image clarity at the corresponding azimuth angles that have been acquired in step S3803, respectively.

The procedure for calculating the two-dimensional distribution of the specular reflectance Rs in step S2909 will be described. FIG. 26C is a flowchart illustrating the procedure for acquiring the two-dimensional distribution of the specular reflectance Rs. First, in step S3201, the information processing apparatus 14 acquires the two-dimensional distribution of the bias information Cs with the diffuse reflection component subtracted therefrom. The value of Cs is calculated with use of the above-described equation (53). In the equation (53), Csmp represents the pixel value in the bias distribution acquired in step S2905, and Cstd represents the pixel value in the bias distribution for the reference diffuse reflection surface that has been acquired in step S2901. $Rd_{smp}$ represents the pixel value in the two-dimensional distribution of the diffuse reflectance Rd that has been acquired in step S2906.

In step S3202, the information processing apparatus 14 acquires the two-dimensional distribution of the average value Dave of the functions D with respect to all of the reflection directions. The average value Dave is calculated by referring to the above-described specular refection conversion table and using the known interpolation method based on the pixel values in the two-dimensional distributions of the anisotropy parameters αu and αv that have been acquired in step S2908.

Next, in step S3203, the information processing apparatus 14 acquires the two-dimensional distribution of the bias information Csd corresponding to the reflected light in the specular reflection direction. The bias information Csd is calculated with use of the above-described equation (54). In the equation (54), Cs represents the pixel value in the two-dimensional distribution of Cs that has been acquired in step S3201, the value of Ds is 1, and the average value Dave is the pixel value in the two-dimensional distribution of the average value Dave that has been acquired in step S3202.

In step S3204, the information processing apparatus 14 acquires the two-dimensional distribution of the specular reflectance Rs. The value of Rs is calculated with use of the above-described equation (55). In the equation (55), Csd represents the pixel value in the two-dimensional distribution of Csd that has been acquired in step S3203, and $Cstd_s$ represents the pixel value in the bias distribution for the reference specular reflection surface that has been acquired in step S2901.

By this processing, the information processing apparatus 14 can calculate the two-dimensional distributions of the parameters Rd, Rs, Nv, φu, αu, and αv in the reflection model.

Figure 27:
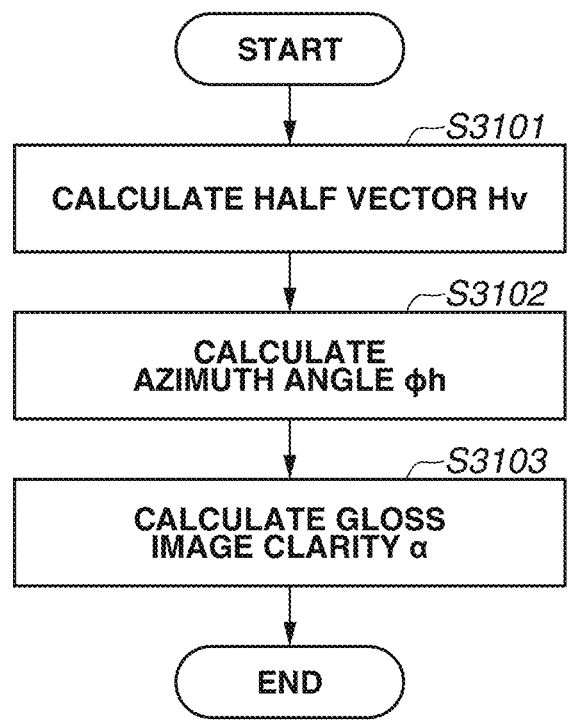
FIG. 27 is a flowchart illustrating a procedure for calculating gloss image clarity a in a reflection model.

Processing for calculating the reflection model with use of the parameters acquired from the measurement system 2500 according to the seventh exemplary embodiment will be described. The processing that will be described below can reproduce the SVBRDF of the measurement object 15 by being performed by an external information processing apparatus that has received the parameters from the measurement system 2500. FIG. 27 is a flowchart illustrating the processing for calculating the reflection model expressing the gloss image clarity. In step S3101, the external information processing apparatus calculates the half vector Hv, which is the bisection direction between the vector ωi indicating the illumination direction and the vector ωo indicating the observation direction, with use of the following equation (64).

$$Hv = \frac{(\omega i + \omega o)}{|\omega i + \omega o|} \quad (64)$$

In this equation (64), $|\omega i+\omega o|$ indicates a size of a vector $(\omega i+\omega o)$.

In step S3102, the external information processing apparatus calculates an azimuth angle component φh of the half vector Hv with use of the following equation (65).

$$\varphi h = \arctan(Hv_y/Hv_x) \quad (65)$$

In the equation (65), $Hv_x$ and $Hv_y$ are an X component and a Y component of the vector Hv, respectively. In step S3103, the external information processing apparatus calculates the gloss image clarity α corresponding to the azimuth angle φh with use of the following equation (66).

$$\alpha = \frac{(\alpha w \times \alpha v)}{\sqrt{\alpha v^2 \times (\cos(\varphi h))^2 + \alpha u^2 \times (\sin(\varphi h))^2}} \quad (66)$$

θg in the above-described equation (52) represents an angle formed between the half vector Hv and the vector Nv indicating the optical normal direction, and is provided as indicated by the following equation (67).

$$\theta g = \arccos(Hv \cdot Nv) \quad (67)$$

As described above, according to the reflection model, the intensity of the reflected light observed under an arbitrary illumination direction and an arbitrary observation direction can be calculated from the parameters Rd, Rs, φu, αu, αv, and Nv measured by the present measurement apparatus. Further, the reflected light when the measurement object 15 is illuminated from a plurality of directions can be acquired by adding reflected light beams leading from respective light beams in the individual illumination directions. Therefore, the reflected light observed under an arbitrary illumination condition can be calculated.

In the above-described manner, according to the measurement apparatus according to the present exemplary embodiment, the SVBRDF can be acquired from the captured images acquired by carrying out the imaging seventeen times at least.

In the above-described exemplary embodiments, the illumination apparatus 11 has been described as including the point light sources arrayed on the flat surface or in the straight line by way of example, but the point light sources may be arrayed on a curved surface or in a curved line. Even in the case where the point light sources are arrayed on the flat surface or in the straight line, this flat surface or straight line does not have to be arranged in parallel with the measurement surface. In this case, the flexibility of the shape of the illumination apparatus 11 increases, and thus the measurement apparatus can be smaller in size. The light source of the illumination apparatus 11 may be a monochrome light source or an RGB color light source. The light source of the illumination apparatus 11 may be a multi-band color light source or a spectroscopic light source. In the case where the measurement apparatus employs the illumination apparatus 11 based on the RGB color light source, the multi-band color light source, or the spectroscopic light source, the gloss intensity can be acquired color by color. For example, the employment of the illumination apparatus 11 based on the RGB color light source allows the gloss intensity to be acquired for each of three R, G, and B bands, and the employment of the illumination apparatus 11 based on the spectroscopic light source allows the gloss intensity to be acquired wavelength by wavelength. The imaging apparatus 12 may be a monochrome camera or may be an RGB color camera. The imaging apparatus 12 may be a multi-band camera, or may be a spectroscopic camera. Similarly to the illumination apparatus 11, the gloss intensity can be acquired color by color in the case where the measurement apparatus employs the RGB color camera, the multi-band camera, or the spectroscopic camera. The imaging apparatus 12 is not limited to the two-dimensional sensor, such as the CCD sensor and the CMOS sensor, and may be an imaging apparatus including a line sensor. The lens is not limited to the telecentric lens, and does not have to be the lens mounted at the position that satisfies the Scheimpflug principle. For example, the lens may be configured in such a manner that a wide-angle lens is used as the lens, the lens is set so as to cause the optical axis thereof to extend in parallel with the direction normal to the measurement surface, and the measurement surface offset from the center of the optical axis is imaged on the sensor surface. The illumination image is not limited to the sinusoidal pattern. The illumination image may be a different pattern as long as it is a periodic function. For example, the illumination image may be a triangular wave pattern. The measurement apparatus has been described as outputting the optical normal direction by way of example, but may be configured to output the reflection direction where the intensity of the reflected light is maximized when the measurement object 15 is illuminated from a predetermined illumination direction. Further or alternatively, the measurement apparatus may be configured to output the illumination direction where the intensity of the received light is maximized of when the light is received in a predetermined light reception direction. The output value of the direction may be the zenith angle and the azimuth angle, or may be a vector value in a three-dimensional space. In this case, the two-dimensional distribution of the optical normal direction is an image storing therein values of Xvn, Yvn, and Zvn at each of the pixels. Such image data is used as a normal map, which is texture data in computer graphics. In this case, values of an X component and a Y component in the vector (a range from −1 to 1) are associated with 0 to 255 of an R signal and a G signal, respectively, and a value of a Z component (a range from 0 to 1) is associated with 0 to 255 of a B signal, according to, for example, the following equations (67) to (69).

$$R = (Xvn+1)/2 \times 255 \quad (68)$$

$$G = (Yvn+1)/2 \times 255 \quad (69)$$

$$B = Zvn \times 255 \quad (70)$$

The feature quantity of the appearance calculated from the two-dimensional distribution of the optical normal direction and the gloss intensity distribution is not limited to the normal direction distribution image, the normal direction density distribution, and the brightness information. For example, the measurement apparatus may be configured to calculate and output an average value, a standard deviation, and/or a skewness of the zenith angles of the optical normal directions. The measurement apparatus may be configured to allow a feature quantity calculation function to be added as an add-in. In this case, the measurement apparatus is equipped with a function of registering and deleting an add-in module, a function of outputting data indicating the two-dimensional distribution of the optical normal direction and the gloss intensity distribution to this module, and a function of inputting the feature quantity calculated by this module. The feature quantity calculation module added as the add-in has a function of calculating a feature quantity including one or a plurality of value(s) based on the data indicating the two-dimensional distribution of the optical normal direction and the gloss intensity distribution. The measurement apparatus may be configured to register the measurement result and the intermediate data of the processing with a server in the Internet via the network I/F.

The present invention can also be realized by processing that supplies a program capable of achieving one or more function(s) of the above-described exemplary embodiments to a system or an apparatus via a network or a storage medium, and causes one or more processor(s) in a computer of the system or apparatus to read out and execute the program. The present invention can also be realized with use of a circuit capable of achieving one or more function(s).

According to the above-described exemplary embodiments, the reflection characteristic of the object can be measured with the simple structure.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-009305, filed Jan. 20, 2016, No. 2016-009310, filed Jan. 20, 2016, No. 2016-218206, filed Nov. 8, 2016, and No. 2016-218207, filed Nov. 8, 2016, which are hereby incorporated by reference herein in their entirety.

What is claimed is:

1. A measurement apparatus comprising:
an illumination unit configured to illuminate a measurement object with use of a plurality of point light sources configured to emit light based on illumination images modulated according to periodic functions out of phase with one another;
an imaging unit configured to image the measurement object illuminated based on the illumination images;
a first calculation unit configured to calculate phase information of a change in a luminance value at each pixel based on a plurality of images captured by the imaging unit; and
a first acquisition unit configured to acquire, from the phase information, a maximum reflection direction where a reflection direction is maximized on the measurement object.

2. The measurement apparatus according to claim 1, wherein the first calculation unit approximates the change in the luminance value at each of the pixels in the plurality of images to the periodic function used by the illumination unit, and calculates a phase difference of the fitted periodic function.

3. The measurement apparatus according to claim 1, wherein the first acquisition unit identifies a point light source located in an illumination direction where a reflection intensity is maximized at a measurement point measured by each of the pixels among the plurality of point light sources based on the phase information, and calculates the maximum reflection direction based on a position of the identified point light source.

4. The measurement apparatus according to claim 1, wherein the illumination unit is a surface light source including the plurality of point light sources on a flat surface, and displays the plurality of illumination images while switching them.

5. The measurement apparatus according to claim 1, wherein the plurality of illumination images is formed in such a manner that a luminance value at each of pixel positions is modulated along the periodic functions, and each of the plurality of illumination images is a periodic pattern.

6. The measurement apparatus according to claim 1, wherein the illumination unit irradiates the measurement object based on the illumination images, the illumination images being classified into two groups in which respective phases change in directions orthogonal to each other, and
wherein the first calculation unit calculates the phase information for each of the directions.

7. The measurement apparatus according to claim 1, wherein the illumination unit includes a display.

8. The measurement apparatus according to claim 1, further comprising a second calculation unit configured to calculate a reflection intensity in the maximum reflection direction based on the plurality of images.

9. The measurement apparatus according to claim 1, further comprising a generation unit configured to calculate a direction normal to a surface where the maximum reflection direction and an illumination direction corresponding to the maximum reflection direction are in a specular reflection relationship with each other as an optical normal direction, and generate an image in which a two-dimensional distribution of the optical normal direction is colored according to the optical normal direction.

10. The measurement apparatus according to claim 9, further comprising a second acquisition unit configured to acquire a distribution of a density of the optical normal direction.

11. The measurement apparatus according to claim 10, further comprising a third acquisition unit configured to acquire brightness information based on the distribution.

12. A non-transitory computer-readable storage medium storing a program that causes a computer to perform a method comprising:
   illuminating a measurement object with use of a plurality of point light sources configured to emit light based on illumination images modulated according to periodic functions out of phase with one another;
   imaging the measurement object illuminated based on the illumination images;
   calculating phase information of a change in a luminance value at each of pixels based on a plurality of images captured in the imaging; and
   acquiring, from the phase information, a two-dimensional distribution of an optical normal direction according to a maximum reflection direction where a reflection direction is maximized on the measurement object.

13. A measurement method comprising:
   illuminating a measurement object with use of a plurality of point light sources configured to emit light based on illumination images modulated according to periodic functions out of phase with one another;
   imaging the measurement object illuminated based on the illumination images;
   calculating phase information of a change in a luminance value at each of pixels based on a plurality of images captured in the imaging; and
   acquiring, from the phase information, a two-dimensional distribution of an optical normal direction according to a maximum reflection direction where a reflection direction is maximized on the measurement object.

14. A measurement apparatus comprising:
   an illumination unit configured to illuminate a measurement object with use of a plurality of point light sources configured to emit light based on illumination images modulated, according to periodic functions, out of phase with one another;
   an imaging unit configured to image the measurement object illuminated based on the illumination images;
   a first calculation unit configured to calculate amplitude information of a change in a luminance value at each of pixels based on a plurality of images captured by the imaging unit; and
   a first acquisition unit configured to acquire, from the amplitude information, a two-dimensional distribution of gloss image clarity of the measurement object.

15. The measurement apparatus according to claim 14, wherein the first calculation unit approximates the change in the luminance value at each of the pixels in the plurality of images to the periodic function used by the illumination unit, and calculates an amplitude of the fitted periodic function.

16. The measurement apparatus according to claim 14, wherein the first acquisition unit carries out a conversion into a parameter representing the gloss image clarity at a measurement point measured by each of the pixels based on the amplitude information.

17. The measurement apparatus according to claim 14, wherein the illumination unit is a surface light source including the plurality of point light sources on a flat surface, and displays the plurality of illumination images while switching them.

18. The measurement apparatus according to claim 14, wherein the plurality of illumination images is formed in such a manner that a luminance value at each of pixel positions is modulated along the periodic functions, and each of the plurality of illumination images is a periodic pattern.

19. The measurement apparatus according to claim 14, wherein the illumination unit includes a display.

20. The measurement apparatus according to claim 14, further comprising a second acquisition unit configured to acquire a two-dimensional distribution of a parameter expressing gloss anisotropy from two-dimensional distributions of a plurality of kinds of gloss image clarity, each of which is the gloss image clarity.

21. The measurement apparatus according to claim 20, further comprising a third acquisition unit configured to acquire an image indicating a distribution of the gloss anisotropy, which is a color image according to an azimuth angle where the gloss image clarity is minimized or maximized, and the gloss image clarity at this azimuth angle and an azimuth angle orthogonal to this azimuth angle from the two-dimensional distribution of the parameter expressing the gloss anisotropy.

22. A non-transitory computer-readable storage medium storing a program that causes a computer to perform a method comprising:
   illuminating a measurement object with use of a plurality of point light sources configured to emit light based on illumination images modulated according to periodic functions out of phase with one another;
   imaging the measurement object illuminated based on the illumination images;
   calculating amplitude information of a change in a luminance value at each of pixels based on a plurality of images captured in the imaging; and
   acquiring, from the amplitude information, a two-dimensional distribution of gloss image clarity of the measurement object.

23. A measurement method comprising:
   illuminating a measurement object with use of a plurality of point light sources configured to emit light based on illumination images modulated according to periodic functions out of phase with one another;
   imaging the measurement object illuminated based on the illumination images;
   calculating amplitude information of a change in a luminance value at each of pixels based on a plurality of images captured in the imaging; and
   acquiring, from the amplitude information, a two-dimensional distribution of gloss image clarity of the measurement object.

* * * * *